United States Patent
Feinberg

(10) Patent No.: US 10,260,067 B2
(45) Date of Patent: *Apr. 16, 2019

(54) ENHANCING DERMAL WOUND HEALING BY DOWNREGULATING MICRORNA-26A

(71) Applicant: The Brigham and Women's Hospital, Inc., Boston, MA (US)

(72) Inventor: Mark W. Feinberg, Newton, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/515,927

(22) PCT Filed: Oct. 1, 2015

(86) PCT No.: PCT/US2015/053531
§ 371 (c)(1),
(2) Date: Mar. 30, 2017

(87) PCT Pub. No.: WO2016/054399
PCT Pub. Date: Apr. 7, 2016

(65) Prior Publication Data
US 2017/0298353 A1 Oct. 19, 2017

Related U.S. Application Data

(60) Provisional application No. 62/058,331, filed on Oct. 1, 2014.

(51) Int. Cl.
| | | |
|---|---|---|
| C07H 21/02 | (2006.01) | |
| C07H 21/04 | (2006.01) | |
| A61K 48/00 | (2006.01) | |
| C12N 15/113 | (2010.01) | |
| A61K 31/7105 | (2006.01) | |
| A61K 9/00 | (2006.01) | |
| A61K 31/712 | (2006.01) | |

(52) U.S. Cl.
CPC .......... *C12N 15/113* (2013.01); *A61K 9/0021* (2013.01); *A61K 31/712* (2013.01); *A61K 31/7105* (2013.01); *C12N 2310/113* (2013.01); *C12N 2310/141* (2013.01); *C12N 2310/3231* (2013.01)

(58) Field of Classification Search
CPC .. C12N 15/113; C12N 2310/11; A61K 31/713
See application file for complete search history.

(56) References Cited

U.S. PATENT DOCUMENTS

| | | | | |
|---|---|---|---|---|
| 2013/0064810 A1* | 3/2013 | Wendel | ............ | C12N 15/113 424/130.1 |
| 2013/0302293 A1* | 11/2013 | Webster | ............ | C12N 5/0647 424/93.21 |
| 2014/0121262 A1 | 5/2014 | Feinberg et al. | | |

FOREIGN PATENT DOCUMENTS

| | | | | |
|---|---|---|---|---|
| WO | WO 2009/100029 A1 * | 8/2009 | .......... | C12N 15/113 |
| WO | WO 2010/129672 A1 * | 11/2010 | .......... | C12N 15/113 |
| WO | 2014/152795 | 9/2014 | | |

OTHER PUBLICATIONS

Barrientos et al., "Growth factors and cytokines in wound healing," Wound Repair Regen, 2008, 16:585-601.
Blakytny and Jude, "The molecular biology of chronic wounds and delayed healing in diabetes," Diabetic Medicine, Jun. 2006, 23:594-608.
Bonauer et al., "MicroRNA-92a controls angiogenesis and functional recovery of ischemic tissues in mice," Science, Jun. 2009, 324:1710-1713.
Bonauer et al., "Vascular microRNAs," Curr Drug Targets, Aug. 2010, 11:943-949.
Brem et al., "Wound-healing protocols for diabetic foot and pressure ulcers," Surgical Technology International, 2003, 11:85-92.
Caporali et al., "Deregulation of microRNA-503 contributes to diabetes mellitus-induced impairment of endothelial function and reparative angiogenesis after limb ischemia," Circulation, Jan. 2011, 123:282-291.
Chan et al., "Downregulation of endothelial microRNA-200b supports cutaneous wound angiogenesis by desilencing GATA binding protein 2 and vascular endothelial growth factor receptor 2," Arteriosclerosis, Thrombosis, and Vascular Biology, Jun. 2012, 32:1372-1382.
Chen and Gorski, "Regulation of angiogenesis through a microRNA (mir-130a) that down-regulates antiangiogenic homeobox genes gax and hoxa5," Blood, Feb. 2008, 111:1217-1226.
Cross and Claesson-Welsh, "FGF and VEGF function in angiogenesis: Signalling pathways, biological responses and therapeutic inhibition," Trends in Pharmacological Sciences, Apr. 2001, 22:201-207.
Dang et al., "MicroRNA-26a regulates tumorigenic properties of EZH2 in human lung carcinoma cells," Cancer Genetics, Mar. 2012, 205:113-123.
Erba et al., "Angiogenesis in wounds treated by microdeformational wound therapy," Ann Surg, Feb. 2011, 253:402-409.
Falanga, "Wound healing and its impairment in the diabetic foot," Lancet, Nov. 2005, 366:1736-1743.
Fasanaro et al., "MicroRNA-210 modulates endothelial cell response to hypoxia and inhibits the receptor tyrosine kinase ligand ephrin-a3," J Biol Chem, Jun. 2008, 283:15878-15883.
Galiano et al., "Topical vascular endothelial growth factor accelerates diabetic wound healing through increased angiogenesis and by mobilizing and recruiting bone marrow-derived cells," The American Journal of Pathology, Jun. 2004, 164:1935-1947.
Goumans et al., "Balancing the activation state of the endothelium via two distinct TGF-β type I receptors," The EMBO Journal, Apr. 2002, 21:1743-1753.
Greene et al., "Microdeformational wound therapy: Effects on angiogenesis and matrix metalloproteinases in chronic wounds of 3 debilitated patients," Ann Plast Surg, Apr. 2006, 56:418-422.
Icli et al., "MicroRNA-26a regulates pathological and physiological angiogenesis by targeting BMP/SMAD1 signaling," Circ Res, Nov. 2013, 113: 1231-1241.

(Continued)

*Primary Examiner* — Amy H Bowman
(74) *Attorney, Agent, or Firm* — Fish & Richardson P.C.

(57) ABSTRACT

Methods for enhancing wound healing, e.g., in diabetic subjects, by administering an antagonist of miR-26a, e.g., an inhibitory nucleic acid that targets miR-26a.

14 Claims, 15 Drawing Sheets

Specification includes a Sequence Listing.

(56) References Cited

OTHER PUBLICATIONS

International Preliminary Report on Patentability in International Application No. PCT/US2015/053531, dated Apr. 13, 2017, 7 pages.
Jin et al., "MicroRNA-99 family targets AKT/mTOR signaling pathway in dermal wound healing," PloS One, May 2013, 8:e64434 (9 pages).
Kolluru et al., "Endothelial dysfunction and diabetes: Effects on angiogenesis, vascular remodeling, and wound healing," International Journal of Vascular Medicine, 2012, 2012:918267 (31 pages).
Lucas et al., "Differential roles of macrophages in diverse phases of skin repair," J Immunol, 2010, 184:3964-3977.
Maruyama et al., "Decreased macrophage number and activation lead to reduced lymphatic vessel formation and contribute to impaired diabetic wound healing," The American Journal of Pathology, 2007, 170:1178-1191.
Menghini et al., "MicroRNA 217 modulates endothelial cell senescence via silent information regulator 1," Circulation, Oct. 2009, 120:1524-1532.
Mirza et al., "Selective and specific macrophage ablation is detrimental to wound healing in mice," The American Journal of Pathology, 2009, 175:2454-2462.
Miyazono and Miyazawa, "Id: A target of bmp signaling," Science's STKE, Sep. 2002, 2002:pe40.
Norton et al., Id helix-loop-helix proteins in cell growth and differentiation, Trends in Cell Biology, Feb. 1998, 8:58-65.
Peng et al., "Lack of FGF-7 further delays cutaneous wound healing in diabetic mice," Plast Reconstr Surg, Dec. 2011, 128:673e-684e.
Potente et al., "Basic and therapeutic aspects of angiogenesis," Cell, Sep. 2011, 146:873-887.
Sayed and Abdellatif, "MicroRNAs in development and disease," Physiol Rev, Jul. 2011, 91:827-887.
Shilo et al., "MicroRNA in cutaneous wound healing: A new paradigm," DNA and Cell Biology, Apr. 2007, 26:227-237.
Song et al., "Use of the parabiotic model in studies of cutaneous wound healing to define the participation of circulating cells," Wound Repair Regen, 2010, 18:426-432.
Suarez et al., "Dicer dependent microRNAs regulate gene expression and functions in human endothelial cells," Circ Res, Apr. 2007, 100:1164-1173.
Trautner et al., "Amputations and diabetes: A case-control study," Diabet Med, 2002, 19:35-40.
Van Solingen et al., "Improved repair of dermal wounds in mice lacking microRNA-155," Journal of Cellular and Molecular Medicine, Jun. 2014, 18: 1104-1112.
Wang et al., "The endothelial-specific microRNA mir-126 governs vascular integrity and angiogenesis," Dev Cell, Aug. 2008, 15:261-271.
Watanabe et al., "Vascular permeability factor/vascular endothelial growth factor (VPF/VEGF) delays and induces escape from senescence in human dermal microvascular endothelial cells," Oncogene, 1997, 14:2025-2032.
White and McIntosh, "Topical therapies for diabetic foot ulcers: Standard treatments," Journal of Wound Care, Oct. 2008, 17:426, 428-432.
Zhou et al., "Regulation of angiogenesis and choroidal neovascularization by members of microRNA-23~27~24 clusters," PNAS, May 2011, 108:8287-8292.
Icli et al., "Regulation of impaired angiogenesis in diabetic dermal wound healing by microRNA-26a," Journal of Molecular and Cellular Cardiology, 2016, 91: 151-159.
International Search Report and Written Opinion dated Mar. 2, 2016 in International Application No. PCT/US2015/053531, 14 pgs.

\* cited by examiner

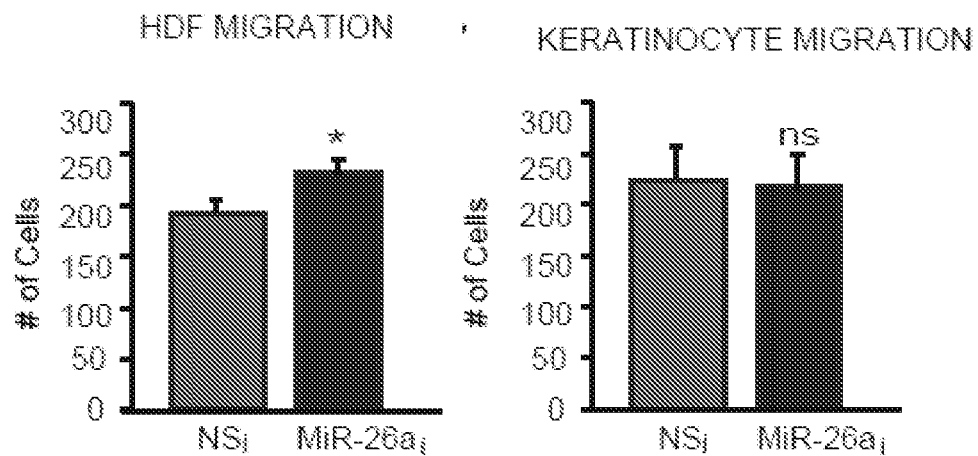
FIG. 6B
FIG. 6C
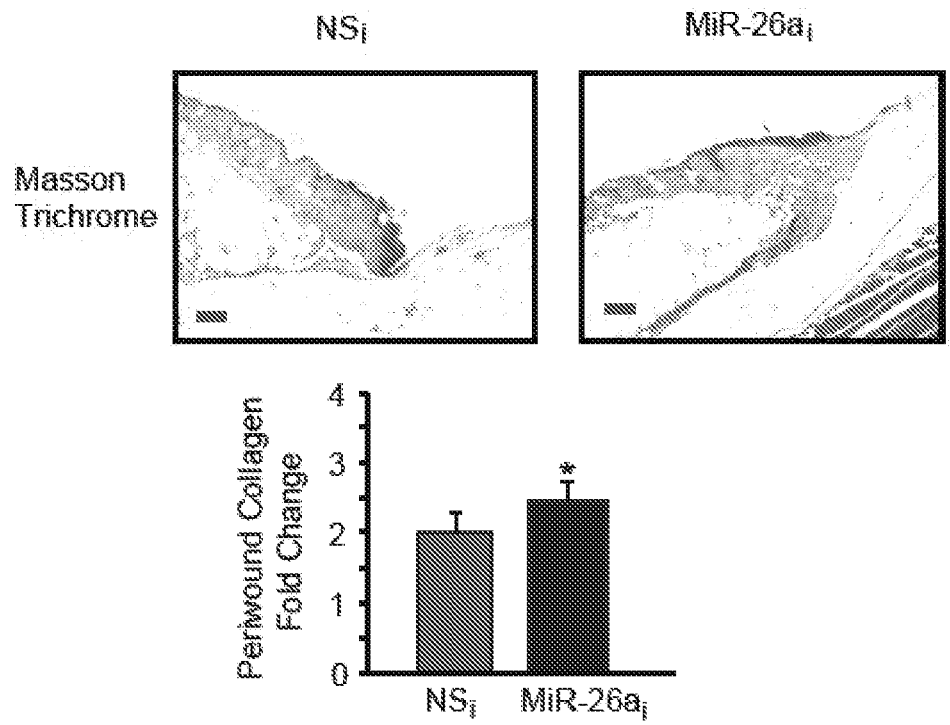
FIG. 7

ENHANCING DERMAL WOUND HEALING BY DOWNREGULATING MICRORNA-26A

CLAIM OF PRIORITY

This application is a U.S. National Phase Application under 35 U.S.C. § 371 of International Patent Application No. PCT/US2015/053531, filed on Oct. 1, 2015, which claims the benefit of U.S. Provisional Application Ser. No. 62/058,331, filed on Oct. 1, 2014. The entire contents of the foregoing are incorporated herein by reference.

FEDERALLY SPONSORED RESEARCH OR DEVELOPMENT

This invention was made with Government support under Grant Nos. HL115141 and HL117994 awarded by the National Institutes of Health. The Government has certain rights in the invention.

TECHNICAL FIELD

Presented herein are methods for enhancing wound healing, e.g., in diabetic subjects, by administering an antagonist of miR-26a, e.g., an inhibitory nucleic acid that targets miR-26a.

BACKGROUND

Diabetes mellitus (DM) is a chronic metabolic disease associated with numerous vascular complications including impaired wound healing. Microvascular complications associated with T2D may lead to, for example, limb amputation and increased risk of mortality. Chronic non-healing ulcers in diabetic patients localized on pressure points of the foot is a major cause of non-traumatic lower leg amputation.[1] These ulcers occur not only in the later stages of diabetes but are also seen in newly diagnosed patients. Accumulating studies focus on promoting angiogenesis, or the formation of blood vessels from pre-existing ones, to promote wound healing in diabetic mouse models.[2-5] Progression of angiogenesis is controlled by a balance between pro- and anti-angiogenic factors. Wound healing requires vascular ECs need to be rapidly activated to migrate to distant sites and proliferate in order to form new primary capillaries from existing ones in response to an angiogenic stimuli.[6] Failure to do so may delay tissue repair in an array of pathological or physiological conditions. Growth factors such as vascular endothelial cell growth factor (VEGF), tumor necrosis factor-α (TNF-α), basic fibroblast growth factor (bFGF), or placenta growth factor (PlGF) are potent regulators of angiogenesis. Impaired EC angiogenic responses have been linked to exacerbation of a wide range of disease states including diabetic wound healing.[7]

SUMMARY

Wound healing is a physiological reparative response to injury and a well-orchestrated process that involves hemostasis, cellular migration, proliferation, angiogenesis, extracellular matrix deposition, and wound contraction and re-epithelialization. However, patients with type 2 diabetes mellitus (T2D) are frequently afflicted with impaired wound healing that can progress into chronic wounds or diabetic ulcers, and may lead to complications including limb amputation. Herein, we describe the role of microRNA-26a (miR-26a) in a diabetic model of wound healing. Expression of miR-26a is rapidly induced in response to high glucose in endothelial cells (ECs). Punch skin biopsy wounding of db/db mice revealed increased expression of miR-26a (~3.5-fold) four days post-wounding compared to that of WT mice. Local administration of a miR-26a inhibitor, LNA-anti-miR-26a, induced angiogenesis (up to ~80%), increased granulation tissue thickness (by 2.5-fold) and accelerated wound closure (53% after nine days) compared to scrambled anti-miR controls in db/db mice. These effects were independent of altered M1/M2 macrophage ratios. Mechanistically, inhibition of miR-26a increased its target gene SMAD1 in ECs nine days post-wounding of diabetic mice. In addition, high glucose reduced activity of the SMAD1-3'-UTR. Diabetic dermal wounds treated with LNA-anti-miR-26a had increased expression of ID1, a downstream modulator or SMAD1, and decreased expression of the cell cycle inhibitor p27. These findings establish miR-26a as an important regulator during the progression of diabetic wound healing by specifically regulating the angiogenic response after injury, and demonstrate that neutralization of miR-26a serves as a novel approach for therapy.

Thus, provided herein are methods for promoting wound healing in a subject that include administering to a subject in need thereof a therapeutically effective amount of an inhibitor of microRNA-26a (miR-26a). Also provided herein are inhibitors of microRNA-26a (miR-26a) for use in promoting wound healing in a subject, or for use in manufacture of a medicament for use in promoting wound healing in a subject.

In some embodiments, the inhibitor of miR-26a is an inhibitory nucleic acid, e.g., an antisense nucleic acid, small interfering RNA (siRNA), or small hairpin RNA (shRNA).

In some embodiments, the inhibitory nucleic acid is modified, e.g., comprises one or more of phosphorothioate bonds, methylphosphonate bonds, peptide nucleic acids, or locked nucleic acid (LNA) molecules.

In some embodiments, the inhibitor is administered locally to the wound, e.g., by injection into the wound or by topical administration onto the wound.

In some embodiments, the subject has diabetes.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 6A-C. Effects of miR-26a deficiency on growth and migration in keratinocytes. (A) Keratinocytes were transfected with miR negative control (NS$_i$) or miR-26a inhibitor (miR-26a$_i$) and cultured in the absence or presence of 30 mM D-glucose. Cells were subjected to cell growth and migration assays. (B) HMVECs transfected with NS$_i$ or miR-26a$_i$ were cultured in the absence or presence of 30 mM D-glucose. On day 3 culture media on the cells were transferred to Boyden chamber and HDFs (B) and keratinocytes (C) were subjected to migration assays. *P<0.05. Results are representative of n=4-6 replicates per group. All data represent means±s.e.m.

FIG. 7. MiR-26a deficiency increases collagen deposition. After two local injections of LNA-anti-miR-26a, db/db mice were wounded by punch biopsy on the upper back and the wounds were collected on day 9 for Masson Trichrome immunostaining. Scale bars, 100 µm. Results are representative of n=7-9 replicates per group. All data represent means±s.e.m.

DETAILED DESCRIPTION

MicroRNAs (miRs) are small evolutionarily conserved, 20-22 nt, non-coding RNAs capable of repressing gene expression at the posttranscriptional level by base pairing at the 3' untranslated regions (3'-UTRs) of mRNA targets and have been found to regulate a variety of physiological and cellular functions in heath and disease.[8, 9] Several reports have identified that miRs regulate various aspects of the angiogenic response to diverse pathophysiological stimuli. For example, miR-126, miR-130a, miR-210, and the miR-23~miR-27~miR-24 cluster promote pro-angiogenic activity, whereas miR-221/miR-222, miR-92a, and miR-217 inhibit angiogenic activity in ECs.[10-16] However, only a few examples of miRs in diabetes-associated angiogenic dysfunction have been reported. For example, miR-126 expression was found to be reduced in CD34$^+$ PBMCs in response to high glucose, an effect that impaired their proangiogenic capacity. In a mouse model of diabetic skin wounding, miR-200b expression was increased in response to TNF-α, which in turn targeted GATA2 and VEGFR2 to supress angiogenesis.[17] Finally, miR-503 is upregulated in response to diabetic conditions, including ischemic limbs, and its neutralization increased blood flow and angiogenesis in diabetic mice with ischemia.[18] Although the studies discussed above investigated various aspects of the role of miRNAs in angiogenic dysfunction in diabetes, the functional role of miRNAs in the context of diabetic wound healing and angiogenesis has not been defined.

Approximately 1 in 4 diabetic subjects will develop a foot ulcer sometime in their lifetime and over two-thirds of these will develop into non-healing wounds despite medical therapy.[24, 25] The normal homeostatic response to wound healing occurs in progressive phases including inflammation, granulation tissue and angiogenesis, and extracellular matrix remodeling; however, in diabetes, an excessive inflammatory response and decreased angiogenesis contribute to the impaired healing response. Herein, we find that miR-26a expression is increased in response to diabetic wound injury and demonstrate that local neutralization of miR-26a promotes wound healing by inducing angiogenesis in diabetic mice, in part, through the BMP/SMAD1 signaling pathway.

Figure 1A:
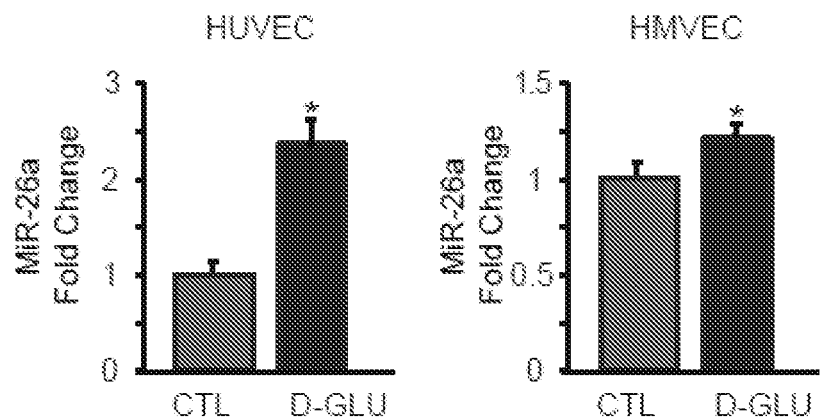
FIGS. 1A-B. MiR-26a is increased in response to high glucose in ECs. Cells were cultured in the absence or presence of 30 mM D-glucose. (A) HUVECs and HMVECs and (B) keratinocytes were evaluated for changes in miR-26a expression levels as quantified by RT-qPCR. *P<0.05. Results are representative of n=4-6 replicates per group. All data represent means±s.e.m.
Figure 3A:
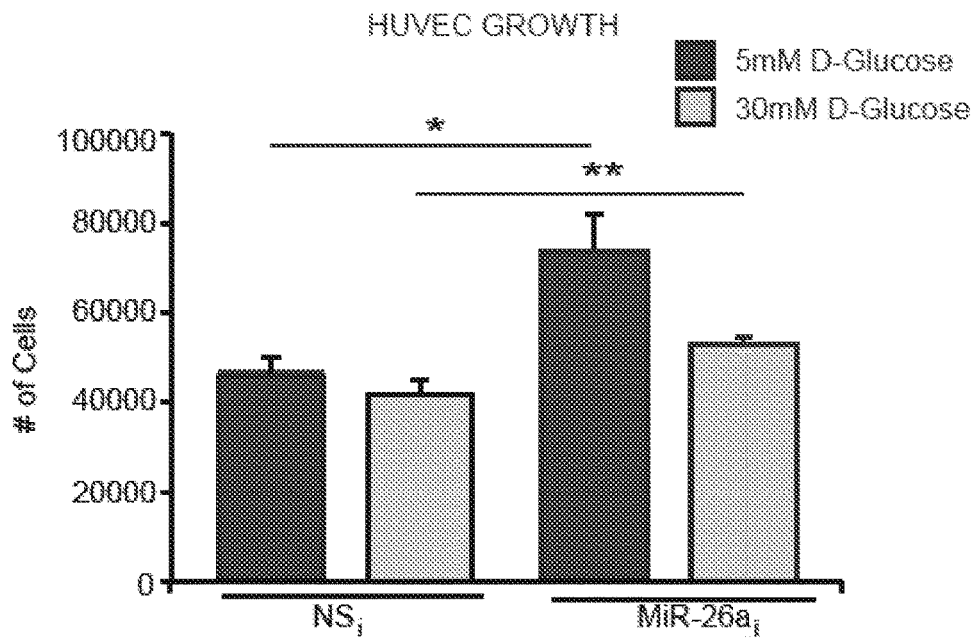
FIGS. 3A-G MiR-26a deficiency rescues impaired growth and migration in ECs, but not dermal fibroblasts. (A-F) HUVECs, HMVECs and HNDFs were transfected with miR negative control (NS$_i$) or miR-26a inhibitor (miR-26a$_i$) and cultured in the absence or presence of 30 mM D-glucose. (A,C,E) Cells were subjected to cell growth assays *P<0.05, **P<0.01; (B,D,F) Cells were subject to migration assay. (G) After two local injections of LNA-anti-miR-26a, db/db mice were wounded by punch biopsy on the upper back and the wounds were collected on day 9 for SM-α-actin by immunostaining. Scale bar 100 µm. Results are representative of n=4-6 replicates per group. All data represent means±s.e.m.
Figure 3B:
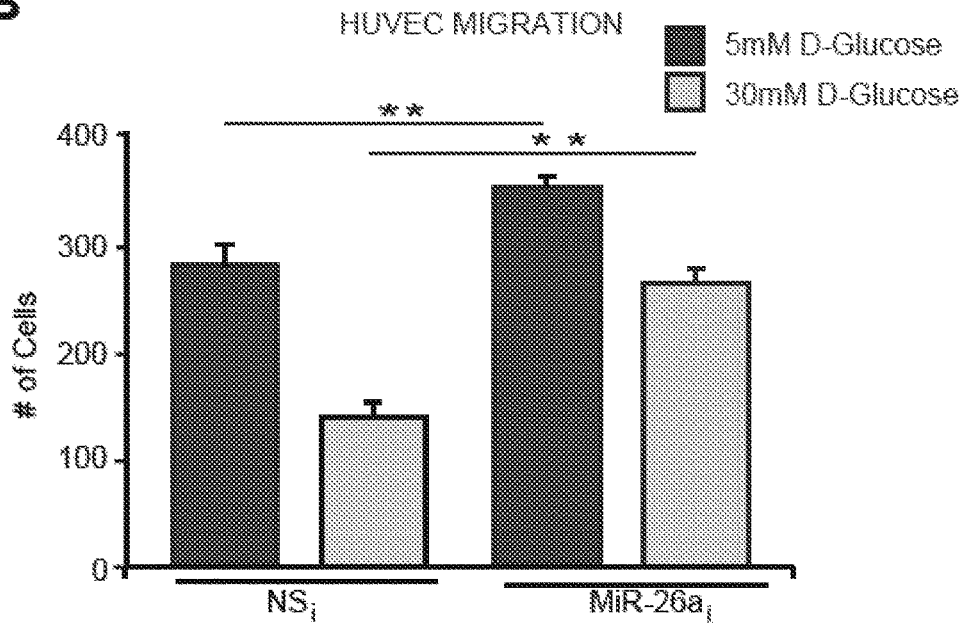
Figure 3C:
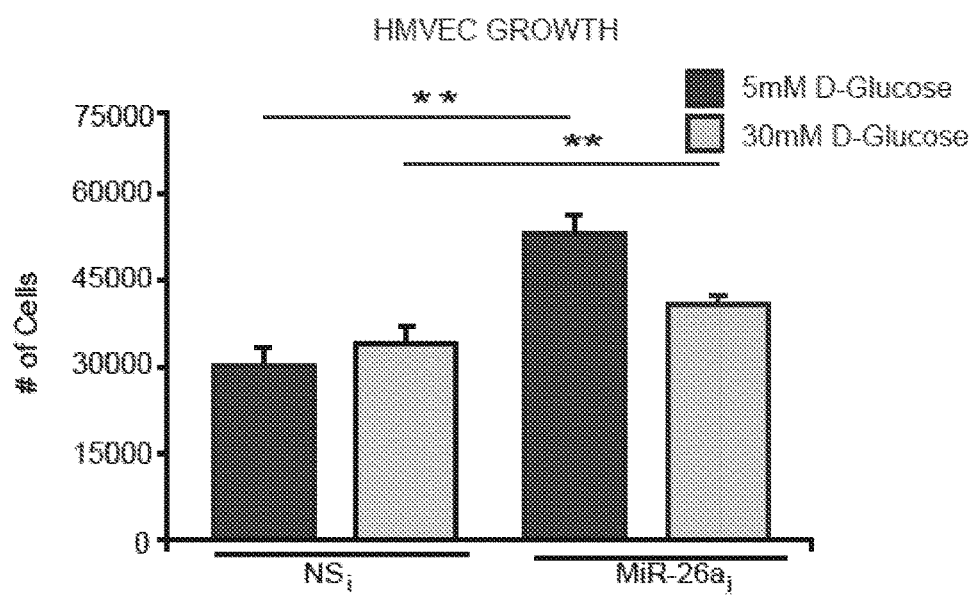
Figure 3D:
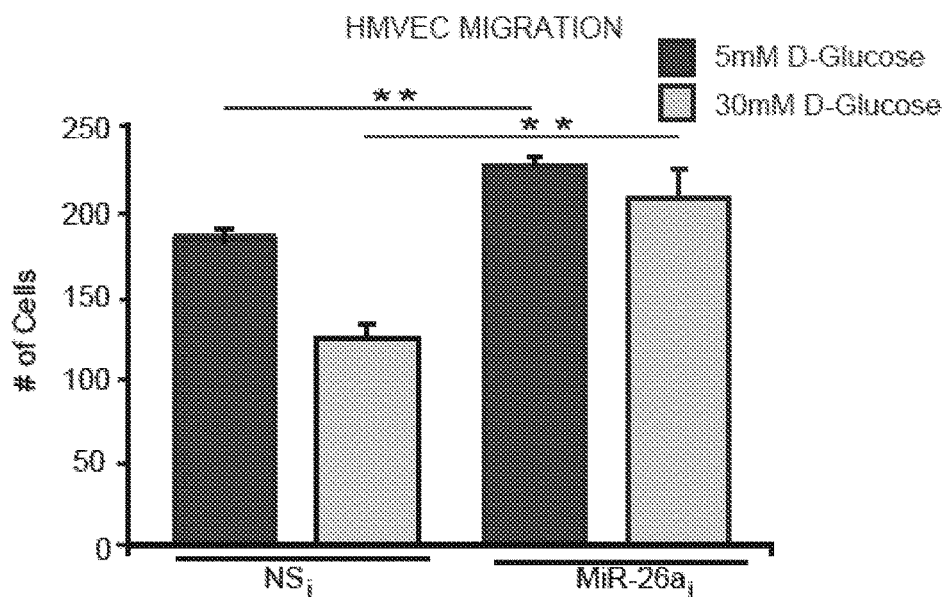
Figure 3E:
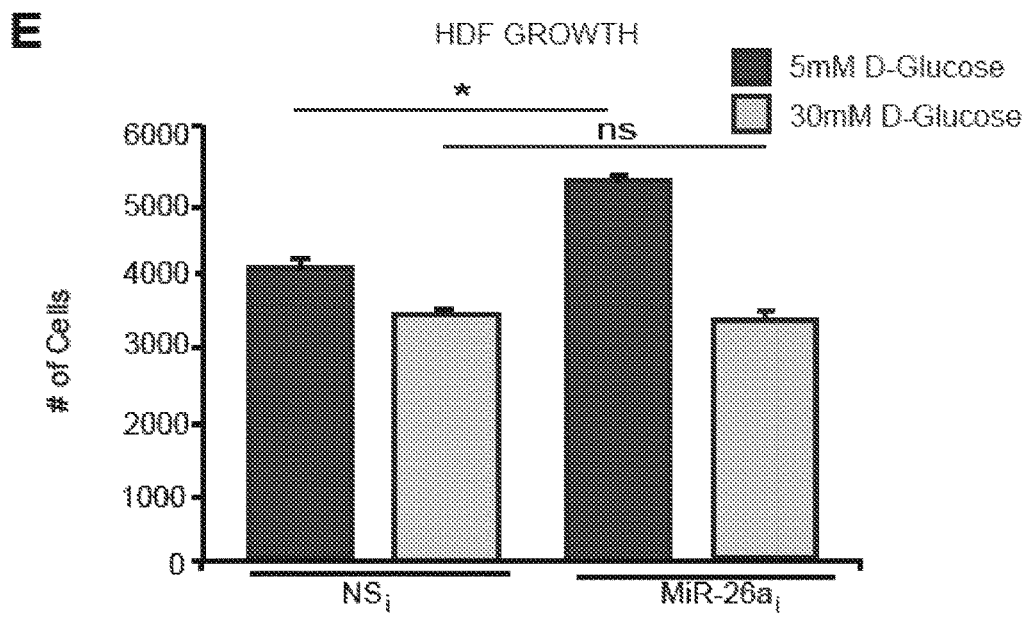
Figure 3F:
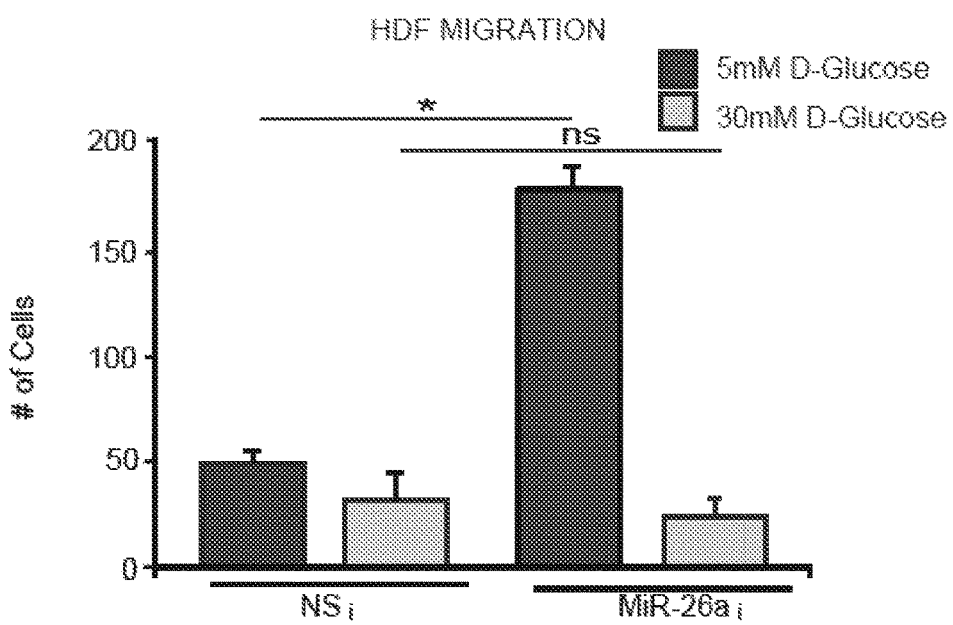
Figure 3G:
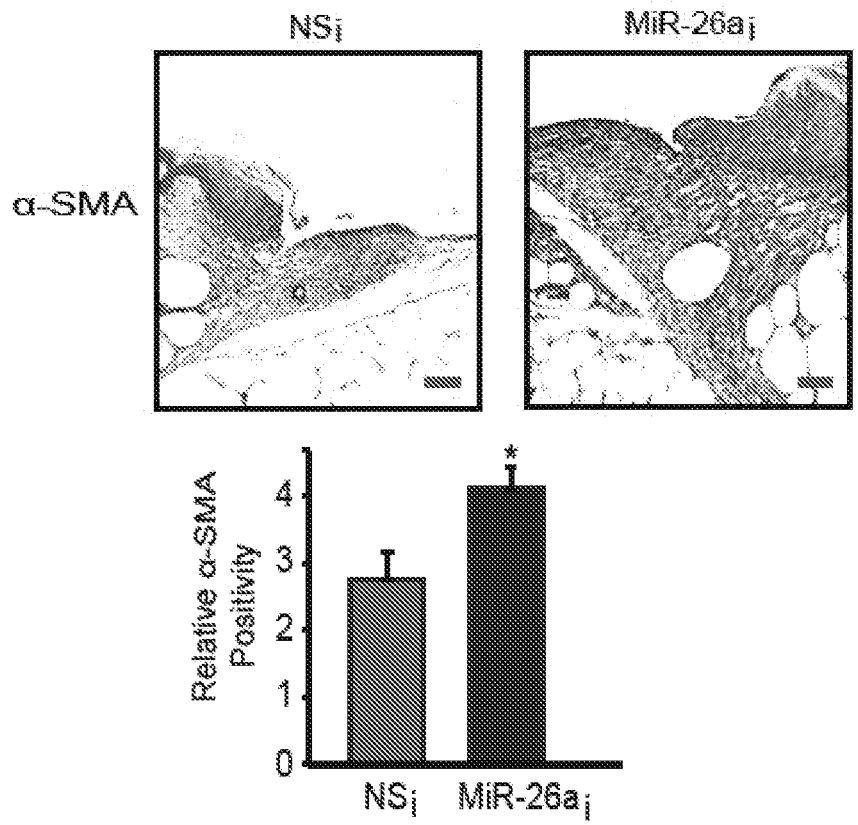
Figure 9:
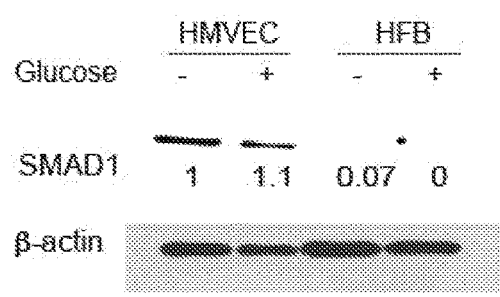
FIG. 9. Expression of SMAD1 in HMVECs and HFBs. HMVECs and HFBs were stimulated with glucose for 24 hours followed by Western analysis of SMAD1 and β-actin. All data represent means±s.e.m

There are a number of cell types such as platelets, keratinocytes, fibroblasts, endothelial, epithelial, and immune cells that orchestrate the complex process of wound healing in response to cytokines and growth factors[19]. Of these cell types, ECs play a central role in angiogenesis where in response to angiogenic stimuli such as VEGF bFGF, or BMPs they migrate and proliferate to form new blood vesels.[26, 27] Indeed, diabetic dermal wounds exhibit reduced angiogenesis and therapeutic enhancement of angiogenesis, for example in response to topical angiogenic growth factors, can facilitate and accelerate wound healing in diabetes.[28, 29, 30] Our studies indicate that diabetic stimuli (e.g. high glucose) markedly increase miR-26a expression in ECs (FIG. 1A). Interestingly, we demonstrated that inhibition of miR-26a rescued impaired growth and migration in the presence of high-glucose in HMVECs and HUVECs. However, there was no effect of anti-miR-26a on dermal fibroblast growth or migration under diabetic conditions (FIG. 3). The lack of functional effects of anti-miR-26a in these cells may be due to the markedly reduced expression of SMAD1 observed in these cells compared to ECs (FIG. 9), or that other potential gene(s) not targeted by miR-26a may be important. Furthermore, the miR-26a neutralization in diabetic wounds did not alter the gene expression profiles of M1 pro-inflammatory or M2 alternatively activated (anti-inflammatory) macrophage markers in diabetic wounds (FIG. 5). Moreover, in response to miR-26a inhibition, there were modest effects on the presence of myofibroblasts in diabetic mice as quantified by SM-α-actin immunostaining (FIG. 3G). Interestingly, cell culture medium from HMVECs transfected with anti-miR-26a and transferred to dermal fibroblasts significantly improved fibroblast cell migration, whereas there were no effects on keratinocytes (FIGS. 6B and 6C). These data suggest that paracrine effects from ECs with miR-26a inhibition may contribute to dermal fibroblast migration and the more modest effects observed on fibroblasts in vivo. These results highlight that neutralization of miR-26a may primarily regulate ECs and the angiogenic phase of wound healing under diabetic conditions. Collectively, these data strongly implicate that local inhibition of miR-26a induces rapid angiogenesis as the dominant mechanism for the increased granulation tissue thickness and wound closure observed.

Figure 4A:
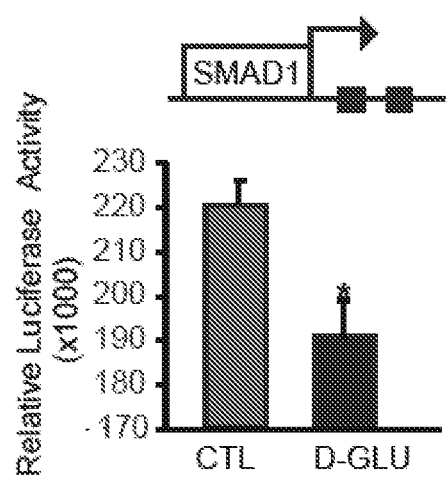
FIGS. 4A-D. MiR-26a targets SMAD1 signaling in diabetic ECs and skin wounds. (A) Luciferase activity of SMAD1-3'UTR normalized to β-gal was quantified in HUVECs stimulated with glucose for 1 hours (n=3 experiments). *P<0.05. Results are representative of n=3 replicates per group and 3 independent experiments. After two local injections, wounds from db/db mice were harvested 9 days post-wounding followed by: (B) RT qPCR for quantitating the expression of SMAD1, ID1 and p27; (C) Western analysis using antibodies to SMAD1 and β-actin; and (D) immunostaining analysis for the quantification of the number of cells co-staining for SMAD1 and CD31. All data represent means±s.e.m. *P<0.05.
Figure 4B:
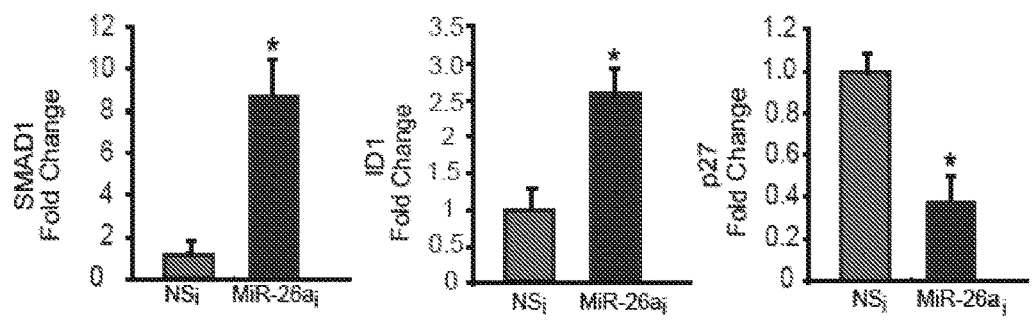
Figure 4C:
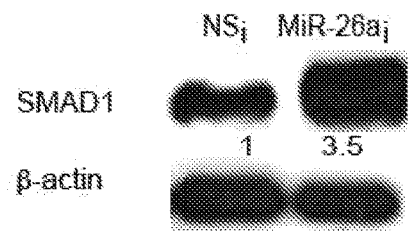
Figure 4D:
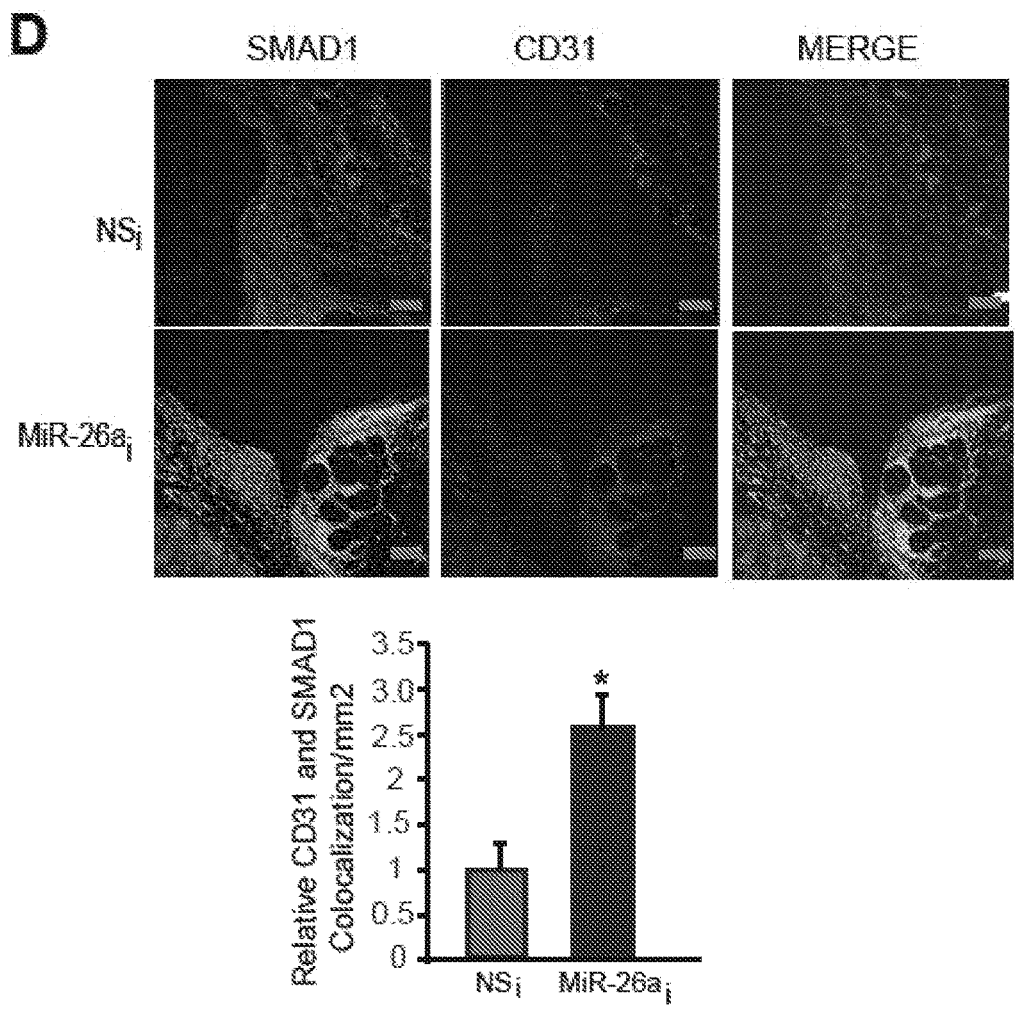

Our findings also demonstrated that miR-26a inhibition in diabetic wounds enhanced BMP/SMAD1 signaling by de-repressing its target gene SMAD1 and, in turn, its downstream regulator ID1, a helix-loop-helix transcription factor that lacks a basic DNA-binding domain and can stimulates EC migration and growth.[31-33] Indeed, in response to miR-26a neutralization, the increased SMAD1 expression co-localized with CD31-positive endothelial cells in diabetic wounds compared to wounds treated with the non-specific LNA-anti-miRs (FIG. 4D). Moreover, the increased expression of ID1 was associated with decreased expression of the cell cycle inhibitor p27 in diabetic wounds in response to miR-26a inhibition. In contrast, our findings revealed that another known miR-26a target EZH2[34] was not differentially regulated by miR-26a in the wounds of the diabetic mice. These findings highlight the growing appreciation that miRNA functional effects are also dictated by cellular context, an effect that is often magnified by discrepancies between primary cells and transformed/tumor cell lines. Future studies will be required to address the relative contribution of other miR-26a targets identified in other cell types to diabetic wound healing.

Accumulating studies suggest a handful of miRNAs may be dysregulated and participate in different pathophysiological phases of diabetic wound healing.[35] For example, miR-155, a miRNA known to functionally regulate diverse aspects of the immune response, was recently found to be induced in diabetic wounds in mice.[36] Deficiency of miR-155 led to a reduced inflammatory response and improved wound closure, an effect associated with increased expression of miR-155 target genes, BCL6, RhoA, SHIP1, and FIZZ1.[36] In addition, expression of members of the miR-99 family were found to be reduced in diabetic wounds; overexpression of this miR family reduced PI3K/Akt signaling and migration and proliferation of keratinocytes, implicating their potential role in the later phase of re-epithelialization[37].

While the expression of a different miRNA, miR-21, was induced late (day 8) in dermal wounds of diabetic mice and miR-21 overexpression increased fibroblast migration in vitro, the role of altering miR-21 expression in diabetic wound healing remains unknown.[35] In addition, the pro-inflammatory cytokine TNF-α increased expression of miR-200b in diabetic wounds, an effect that decreased GATA2 and VEGFR2 and altered the angiogenic response; conversely, miR-200b deficiency attenuated TNF-α's effects and promoted angiogenesis.[17]. Interestingly, miR-26a was among the top profiled miRNAs that increased in the chronic diabetic wound group by array-based screening of plasma samples. Taken together, these examples, coupled with the miR-26a-mediated angiogenic effects observed in our study, subserve the notion that miRNAs exhibit distinct and phase-specific effects during the response to diabetic wound healing.

In summary, our findings establish that miR-26a expression is increased in response to diabetic wound injury and that neutralization of miR-26a confers favorable wound healing properties predominantly mediated by effects on angiogenesis. The miR-26a-mediated effects were associated with increased pro-angiogenic BMP/SMAD1-ID1 signaling in ECs and robust functional effects on diabetic ECs, but not dermal fibroblasts. Furthermore, miR-26a did not alter the M1/M2 macrophage ratio in diabetic wounds highlighting that miRNA-mediated control of the angiogenic phase is sufficient to promote wound healing. Collectively, these findings provide insights to the regulation of angiogenesis in diabetic wound healing by miRNAs and demonstrate that miR26a antagonism ameliorates complications from diabetic wounds.

Promoting Wound Healing

Described herein are methods of promoting wound healing, e.g., in subjects with or without diabetes. In exemplary embodiments, the wound is an ulcer, e.g., a foot ulcer, in a diabetic subject. The present methods can also be used in non-diabetics to promote wound healing. Methods for diagnosing a subject with diabetes are well known in the art.

As used herein a wound is a physical injury to a subject's skin or mucosal tissue, typically caused by a cut, blow, or other impact or trauma, in which the skin or tissue is cut or broken. The wound can be, for example, an accidental wound, e.g., the result of trauma, or the result of intentional cutting such as for a surgical intervention. The wound can also be the result of or contributed to by chronically poor circulation, cold/frostbite, chronic rubbing of the skin, or any other process that results in a break in the skin and/or mucosal tissue.

The methods can include systemic or (more preferably) local delivery of an inhibitory nucleic acid targeting miRNA-26a, e.g., in a pharmaceutical composition as described herein or known in the art, to the wounded area and/or surrounding tissues.

Inhibitory Nucleic Acids Targeting microRNA-26a (miR-26a)

The methods and compositions described herein can include nucleic acids that targets (specifically binds, or is complementary to) miR-26a. Inhibitory nucleic acids useful in the present methods and compositions include antisense oligonucleotides (e.g., antimirs), small interfering RNA (siRNA), small hairpin RNA (shRNA), molecules comprising modified bases, locked nucleic acid molecules (LNA molecules), peptide nucleic acid molecules (PNA molecules), and other oligomeric compounds or oligonucleotide mimetics that hybridize to at least a portion of the target nucleic acid and inhibit its function. Alternatively or in addition, vector-based miRNA inhibitors such as microRNA sponges and microRNA Decoy is a powerful tool; both can inhibit specifically an entire miRNA seed family (Bak et al., 2013. RNA 19, 280-293.).

The sequence of mature has-miR-26a is as follows: UUCAAGUAAUCCAGGAUAGGCU (SEQ ID NO:1)

The sequence and structure of hsa-miR-26a-1 precursor (SEQ ID NO:2) is as follows:

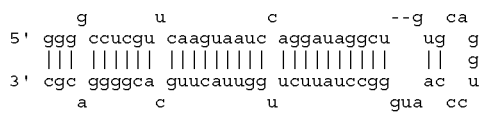

The sequence and structure of hsa-miR-26a-2 precursor (SEQ ID NO:3) is as follows:

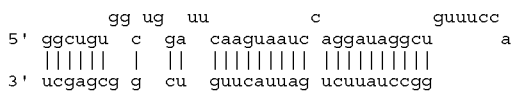

The linear sequences for has-miR-26a-1 and -2 are GUG-GCCUCGUUCAAGUAAUCCAGGAUAGGCUGUGCA-GGUCCCAAUGGGCC UAUUCUUGGUUACUUG-CACGGGGACGC (SEQ ID NO:2) and GGCUGUGGCUGGAUUCAAGUAAUCCAGGAUAG-GCUGUUUCCAUCUGUGAG GCCUAUUC-UUGAUUACUUGUUUCUGGAGGCAGCU (SEQ ID NO:3), respectively. The sequences for miR-26a homologs from other species are known in the art.

In some embodiments, the inhibitory nucleic acids are 7 to 50, 7 to 20, 7 to 25, 10 or 13 to 50, or 10 or 13 to 30 nucleotides (nts) in length, or as short as 7 or 8 up to the entire length of the target sequence (e.g., 7 to 22, 7 to 77, or 7 to 84 nts for SEQ ID NOs. 1, 2, and 3 respectively). One having ordinary skill in the art will appreciate that this embodies inhibitory nucleic acids having complementary portions of 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more nucleotides in length, or any range therewithin. In some embodiments, the inhibitory nucleic acids are 15 nucleotides in length. In some embodiments, the inhibitory nucleic acids are 12 or 13 to 20, 25, or 30 nucleotides in length. One having ordinary skill in the art will appreciate that this embodies inhibitory nucleic acids having complementary portions of 12, 13, 14, 15, 16, 17, 18, 19, 20, 21, 22, 23, 24, 25, 26, 27, 28, 29 or 30 nucleotides in length, or any range therewithin (complementary portions refers to those portions of the inhibitory nucleic acids that are complementary to the target sequence). In some embodiments, especially those embodiments in which the inhibitory nucleic acid is relatively short, e.g., 7-10 nts long, the inhibitory nucleic acid is complementary to the seed sequence of the miRNA, e.g., UUCAAGU (SEQ ID NO:4).

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position. 100% complementarity is not required.

Routine methods can be used to design an inhibitory nucleic acid that binds to the target sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30-60%. Contiguous runs of three or more Gs or Cs should be avoided where possible (for example, it may not be possible with very short (e.g., about 9-10 nt) oligonucleotides).

In some embodiments, the inhibitory nucleic acid molecules can be designed to target a specific region of the RNA sequence. For example, a specific functional region can be targeted, e.g., a region comprising a known RNA localization motif (i.e., a region complementary to the target nucleic acid on which the RNA acts). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

Once one or more target regions, segments or sites have been identified, e.g., within a sequence known in the art or provided herein, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a RNA molecule, then the inhibitory nucleic acid and the RNA are considered to be complementary to each other at that position. The inhibitory nucleic acids and the RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or precise pairing such that stable and specific binding occurs between the inhibitory nucleic acid and the RNA target. For example, if a base at one position of an inhibitory nucleic acid is capable of hydrogen bonding with a base at the corresponding position of a RNA, then the bases are considered to be complementary to each other at that position. 100% complementarity is not required.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target RNA molecule interferes with the normal function of the target RNA to cause a loss of activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Inhibitory nucleic acids that hybridize to an RNA can be identified through routine experimentation. In general the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids), as well as WO2012/065143, WO2012/087983, and WO2014/025887 (inhibitory nucleic acids targeting non-coding RNAs/supRNAss), all of which are incorporated herein by reference in their entirety.

Antisense Oligonucleotides—Anti-miRs

In some embodiments, the inhibitory nucleic acids are antisense oligonucleotides, e.g., antagomiRs (typically conjugated to cholesterol), antimiRs/blockmiRs, as well as tiny antimiRs (7-8 nts long that target miRNA families by targeting the seed sequence). These antisense oligonucleotides are designed to bind to the target miRNA and (without wishing to be bound by theory) inhibit function. Antisense oligonucleotides of the present invention are complementary nucleic acid sequences designed to hybridize under stringent conditions to an RNA. Thus, oligonucleotides are chosen that are sufficiently complementary to the target, i.e., that hybridize sufficiently well and with sufficient specificity, to give the desired effect. See, e.g., Stenvang et al., Silence. 2012; 3:1; Figueira et al., Acta Physiol (Oxf). 2014 July; 211(3):491-500; Huricha and Rana, Nanomedicine, 9(16): 2545-2555 (2014); Bernardo et al., Future Med Chem. 2015 Sep. 24 (doi:10.4155/fmc.15.107).

siRNA/shRNA

In some embodiments, the nucleic acid sequence that is complementary to an target RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc Natl Acad Sci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific RNA targets within the background of cellular RNA. Such a cleavage event renders the RNA non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $\text{min}^{-1}$ in the presence of saturating (10 rnM) concentrations of $\text{Mg}^{2+}$ cofactor. An artificial "RNA ligase" ribozyme has been shown to catalyze the corresponding self-modification reaction with a rate of about 100 $\text{min}^{-1}$. In addition, it is known that certain modified hammerhead ribozymes that have substrate binding arms made of DNA catalyze RNA cleavage with multiple turn-over rates that approach 100 $\text{min}^{-1}$.

Modified Inhibitory Nucleic Acids

In some embodiments, the inhibitory nucleic acids used in the methods described herein are modified, e.g., comprise one or more modified bonds or bases. A number of modified bases include phosphorothioate, methylphosphonate, peptide nucleic acids, or locked nucleic acid (LNA) molecules. Some inhibitory nucleic acids are fully modified, while others are chimeric and contain two or more chemically distinct regions, each made up of at least one nucleotide. These inhibitory nucleic acids typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5, 220,007; 5,256,775; 5,366,878; 5,403,711; 5,491,133; 5,565,350; 5,623,065; 5,652,355; 5,652,356; and 5,700,922, each of which is herein incorporated by reference. In some embodiments, the modifications are 2' sugar modifications including 2'-O-methyl ribose-modified RNA (2'-OMe), 2'-O-methoxyethyl (2'-MOE), 2'-fluoro (2'-F) and LNA modifications. See, e.g., Bernardo et al., Future Med Chem. 2015 Sep. 24 (doi:10.4155/fmc.15.107).

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2'O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the inhibitory nucleic acid into which they are incorporated more resistant to nuclease digestion than the native oligodeoxynucleotide; these modified oligos survive intact for a longer time than unmodified inhibitory nucleic acids. Specific examples of modified inhibitory nucleic acids include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are inhibitory nucleic acids with phosphorothioate backbones and those with heteroatom backbones, particularly CH2-NH—O—CH2, CH, ~N(CH3)~O~CH2 (known as a methylene(methylimino) or MMI backbone], CH2-O—N(CH3)-CH2, CH2-N(CH3)-N(CH3)-CH2 and O—N(CH3)-CH2-CH2 backbones, wherein the native phosphodiester backbone is represented as O—P—O—CH); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (i.e., peptide bonds, wherein the phosphodiester backbone of the inhibitory nucleic acid is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5, 177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid inhibitory nucleic acid mimetics are described in Wang et al., J. Am. Chem. Soc., 2000, 122, 8595-8602.

Modified inhibitory nucleic acid backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, SCH$_3$, F, OCN, OCH$_3$OCH$_3$, OCH$_3$O(CH$_2$)nCH$_3$, O(CH$_2$)nNH$_2$ or O(CH$_2$)nCH$_3$ where n is from 1 to about 10; Ci to C10 lower alkyl, alkoxyalkoxy, substituted lower alkyl, alkaryl or aralkyl; Cl; Br; CN; CF3; OCF3; O—, S—, or N-alkyl; O—, S—, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an inhibitory nucleic acid; or a group for improving the pharmacodynamic properties of an inhibitory nucleic acid and other substituents having similar properties. A preferred modification includes 2'-methoxyethoxy [2'-O-CH$_2$CH$_2$OCH$_3$, also known as 2'-O-(2-methoxyethyl)] (Martin et al, Helv. Chim. Acta, 1995, 78, 486). Other preferred modifications include 2'-methoxy (2'-O-CH$_3$), 2'-propoxy (2'-OCH$_2$CH$_2$CH$_3$) and 2'-fluoro (2'-F). Similar modifications may also be made at other positions on the inhibitory nucleic acid, particularly the 3' position of the sugar on the 3' terminal nucleotide and the 5' position of 5' terminal nucleotide. Inhibitory nucleic acids may also have sugar mimetics such as cyclobutyls in place of the pentofuranosyl group.

Alternatively or in addition, the modification can be inclusion of N,N-diethyl-4-(4-nitronaphthalene-1-ylazo)-phenylamine ('ZEN'), which when placed near the ends of a 2'-OMe modified oligonucleotide (ZEN-AMO) increased binding affinity and blocked exonuclease degradation as compared to unmodified 2'-OMe oligonucleotides (Lennox et al., Mol. Ther. Nucleic Acids 2, e117 (2013)).

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given inhibitory nucleic acid to be uniformly modified, and in fact more than one of the aforementioned modifications may be incorporated in a single inhibitory nucleic acid or even at within a single nucleoside within an inhibitory nucleic acid.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an inhibitory nucleic acid mimetic that has been shown to have excellent hybridization properties, is referred to as a peptide nucleic acid (PNA). In PNA compounds, the sugar-backbone of an inhibitory nucleic acid is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175, 273; 5, 367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the inhibitory nucleic acid. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717; 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241, 5,391, 723; 5,416,203, 5,451,463; 5,510,475; 5,512,667; 5,514,785; 5, 565,552; 5,567,810; 5,574,142; 5,585,481; 5,587,371; 5,595,726; 5,597,696; 5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Locked Nucleic Acids (LNAs)

In some embodiments, the modified inhibitory nucleic acids (including ASOs) used in the methods described herein comprise locked nucleic acid (LNA) molecules, e.g., including [alpha]-L-LNAs. LNAs comprise ribonucleic acid analogues wherein the ribose ring is "locked" by a methylene bridge between the 2'-oxygen and the 4'-carbon—i.e., inhibitory nucleic acids containing at least one LNA monomer, that is, one 2'-0,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herein.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA; for example, a series of inhibitory nucleic acids of 10-30 nucleotides spanning the length of a target RNA can be prepared, followed by testing for activity. Optionally, gaps, e.g., of 5-10 nucleotides or more, can be left between the LNAs to reduce the number of inhibitory nucleic acids synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of more than four LNA residues, should be avoided where possible (for example, it may not be possible with very short (e.g., about 9-10 nt) inhibitory nucleic acids). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998), Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

See, e.g., Stenvang et al., Silence. 2012; 3:1; Figueira et al., Acta Physiol (Oxf). 2014 July; 211(3):491-500; Huricha and Rana, Nanomedicine, 9(16):2545-2555 (2014); Bernardo et al., Future Med Chem. 2015 Sep. 24 (doi:10.4155/fmc.15.107).

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., Molecular Cloning; A Laboratory Manual 3d ed. (2001); Current Protocols in Molecular Biology, Ausubel et al., eds. (John Wiley & Sons, Inc., New York 2010); Kriegler, Gene Transfer and Expression: A Laboratory Manual (1990); Laboratory Techniques In Biochemistry And Molecular Biology: Hybridization With Nucleic Acid Probes, Part I. Theory and Nucleic Acid Preparation, Tijssen, ed. Elsevier, N.Y. (1993).

Pharmaceutical Compositions

The methods described herein can include the administration of pharmaceutical compositions and formulations comprising an inhibitory nucleic acid that targets miR-26a.

In some embodiments, the compositions are formulated with a pharmaceutically acceptable carrier. The pharmaceutical compositions and formulations can be administered parenterally, topically, orally or by local administration, such as by injection, topical application (e.g., of a lotion, cream, gel, or spray), or other dermal or transdermal application. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., Remington: The Science and Practice of Pharmacy, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered by a topical route, e.g., formulated as solutions, suspensions, emulsions, gels, creams, ointments, pastes, jellies, paints, powders, and aerosols.

In some embodiments, the pharmaceutical compounds can also be delivered as microspheres for slow release into the wound. For example, microspheres can be administered, e.g., topically or via intradermal injection, which slowly release subcutaneously; see Rao (1995) J. Biomater Sci. Polym. Ed. 7:623-645; as biodegradable and topically applied or injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration directly onto the wound. These formulations can comprise a solution of active agent dissolved in a pharmaceutically acceptable carrier. Acceptable vehicles and solvents that can be employed are water and Ringer's solution, an isotonic sodium chloride. In some embodiments, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The compositions and formulations can be delivered by the use of liposomes. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The amount of pharmaceutical composition adequate to accomplish an enhancement of wound healing is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; *Remington: The Science and Practice of Pharmacy,* 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as *Remington: The Science and Practice of Pharmacy,* 21st ed., 2005.

Various studies have reported successful mammalian dosing using complementary nucleic acid sequences. For example, Esau C., et al., (2006) Cell Metabolism, 3(2):87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, non-toxic dose. Another study by Kriitzfeldt J., et al., (2005) Nature 438, 685-689, injected anatgomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg kg-1 LNA-antimiR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., compositions for providing cholesterol homeostasis. For example, the inhibitory nucleic acids can be co-administered with drugs for treating or reducing risk of a disorder described herein.

EXAMPLES

The invention is further described in the following examples, which do not limit the scope of the invention described in the claims.

Examples 1-5

Herein, we identify a unique role for miR-26a in regulating the progression of diabetic wound healing. Specifically, our findings indicate that miR-26a expression is induced in wounds of diabetic mice. Neutralization of miR-26a effectively promoted wound closure and was associated with favorable phenotype features including increased granulation tissue, induction of SMAD1 signaling in ECs, and markedly enhanced angiogenesis. We further identify novel cell-specific functional effects of miR-26a that may underlie these observations. Collectively, these findings indicate that therapeutic inhibition of miR-26a provides a promising treatment for diabetic subjects with impaired dermal wound healing.

Materials and Methods

The following materials and methods were used in the Examples set forth below.

Cell Culture and Transfection

Human umbilical vein endothelial cells (HUVECs) (cc-2159; Lonza, Walkersville, Md.) were cultured in growth media EGM®-2 (cc-3162; Lonza Walkersville, Md.). Human dermal microvascular endothelial cells (HMVECs) (cc-2543; Lonza, Walkersville, Md.) were cultured in growth media EGM®-2-MV (cc-3202; Lonza Walkersville, Md.). Human dermal fibroblasts NHDF) (cc-2511; Lonza, Walkersville, Md.) were cultured in growth media FGM®-2 (cc-3122; Lonza Walkersville, Md.). Cells passaged less than five times were used for all experiments. VEGF-A was obtained from R&D Systems. D-Glucose was obtained from Sigma. For transfection studies, HUVECs were plated at 50,000 cells/well and cultured overnight before being transfected with Lipofectamine™ 2000 transfection reagent (Invitrogen), following manufacturer's instructions. MiRNA negative controls, and miR-26a inhibitor (AM17100; Ambion, Inc.) were transfected in HUVECs at 100 nM concentration except where indicated. Cy™3 labeled-negative control #1 (AM17120; Ambion) was transfected in parallel to assess transfection efficiency which was >90%. For functional studies, HUVECs, HMVECs, HFBs or Kerationocytes were cultured with 5 mM or 30 mM D-Glucose for 72 hours. For reporter studies, HUVECs were plated (50,000/well) in triplicate on a 12-well plate, grown to 70-80% confluency, and transfected with 800 ng of the indicated reporter constructs and 200 ng β-galactosidase (β-gal) expression plasmids. Transfected cells were collected in 200 μl Reporter Lysis Buffer (Promega). The activity of luciferase and β-gal were measured. Each reading of luciferase activity was normalized to the β-gal activity read for the same lysate.

Real-Time qPCR

HUVECs were suspended in TRIzol® reagent (Invitrogen) and total RNA and microRNA was isolated using Trizol® reagent (Invitrogen) per manufacturer's instructions. Reverse transcriptions were performed by using miScript Reverse Transcription Kit from Qiagen (218061). Either QuantiTect SYBR Green RT-PCR Kit (204243) or miScript SYBR Green PCR Kit (218073) from Qiagen was used for quantitative real-time qPCR analysis with the Mx3000P Real-time PCR system (Stratagene) following the manufacturer's instructions. Gene-specific primers were used to detect mouse Smad1, ID1, p27, Ym1, Mg12, Arg1, Mrc2, Fizz, IL6, IL12, IL1β and NOS2. To amplify mature miRNA sequences, miScript primer assays for Hs_RN5S1_1 (MS00007574), Hs_miR-26a$_{-1}$ (MS00006559) from Qiagen were used. Samples were normalized to endogenous 5S RNA (human). Fold changes were calculated by ΔΔCt method.

Chemotaxis Assays:

Migration assay was performed using ChemTX multiwell system (Neuro probe Inc, Md.) with 5 mm pore size and 96 well format. HUVECs transfected with miR-26a inhibitor, or non-specific negative controls were cultured for 72 hours before being plated on the upper compartment of the multiwell plate to assess migration. Lower compartments were filled with EBM-2 medium containing VEGF (R&D Systems). The number of cells migrating to the lower chamber was counted using a hemocytometer after 16 hours. Three technical replicated were used per condition and studies were validated in at least 2 independent experiments.

Western Blot Analysis:

HUVECs transfected with miR-26a mimic, miR-26a inhibitor, or non-specific negative controls were cultured for 72 hours. Total cellular protein was isolated by RIPA buffer (50 mM Tris-HCL pH 7.4, 150 mM NaCl, 1% NP-40, 0.5% sodium deoxycholate, 0.1% SDS) supplemented with protease inhibitors (Roche). Cell or tissue debris was removed by centrifugation at 12000 rpm for 10 min. Lysates were separated by 8% or 10% SDS-PAGE gels, transferred to PVDF membranes (Bio-Rad). Protein quantification was performed using the BCA kit (Thermo Scientific) and cellular lysates were subjected to Western blotting using antibodies against SMAD1 (Cell Signaling), EZH2 (Cell Signaling), and β-actin (Cell Signaling). HRP-conjugated goat anti-rabbit or mouse antibody (Santacruz) was used at 1:5000 dilution. ECL assay was performed per manufacturer's instructions (RPN2132; GE Healthcare).

Mast Cell (MC) Staining/Toluidine Staining

In brief, sections were deparaffinized and then hydrated in distilled water. Sections were stained with toluidine blue working solution (Sigma, St. Louis, Mo.) solution for 2-3 minutes and then washed in distilled water. Sections were then briefly dehydrated in 95% and 100% alcohol, air-dried overnight and then analyzed. Intact (non-degranulated) MC were purple in color and contained characteristic granules, while degranulated MC were magenta/violet in color and were devoid of granules. Using the 10× objective, a "hot spot" was chosen (visual field with higher accumulation of MC). The 40× objective was then used to count the number of total, degranulated and non-degranulated cells per visual field (high power field, hpf). The same was done for "non-hot spot" areas. The average for total, degranulated and non-degranulated MC was then calculated. The analysis was performed by two blinded and independent reviewers.

Masson's Trichrome Stain

The manufacturer's protocol (American Mastertech Kit, ATMS Inc., Lodi, Calif.) was followed. In brief, the sections were deparaffinized and then serially hydrated in ethanol. Sections were stained in Bouin's fluid at room temperature overnight. The next day, sections were washed and briefly stained in Weigert's hematoxylin solution. With intermittent rinses, the sections were incubated in Biebrich Scarlet-Acid Fuchsin, phosphomolybdic/phosphotungstic acid, aniline blue, and lastly 1% acetic acid. Sections were dehydrated and coverslips were applied. The 10× objective was used to identify the wound edge and collagen content (blue appearance) was scored with a value of 1-5. The analysis was performed by two blinded and independent reviewers.

In Vivo miR-26a Inhibition and Mouse Experiments

Animal protocols were approved by the Laboratory Animal Care at Harvard Medical School. For diabetic wound healing, male, 8-10 weeks old, db/db mice (Jackson) were injected intradermally with either scrambled control LNA-anti-miR or LNA-anti-miR-26a (Exiqon, Inc) at 50 μM 48 h and 24 h prior to surgery. On day 0 dorsal full-thickness skin wounds (1 cm$^2$) were generated and covered with semi-occlusive dressing (Tegaderm). Images of the wounds were immediately acquired after surgery (day 0) and on days 4 and 9 following the removal of the Tegaderm dressing. Mice were euthanized 9 days post-surgery and the 1×1 cm$^2$ sections of skin surrounding the wound were excised down to fascia. Angiogenesis in wound tissue was analyzed by mouse CD31 staining and isolectin B4 (B-1205; Vector Laboratories, Inc) of the paraffin embedded wound sections as we previously described.[20] Granulation tissue thickness was measured on day 10 using H&E stained sections obtained from the center of the wound. Granulation tissue thickness was defined as the distance of intact tissue from the bottom of the epidermis to the top of the subcutaneous fat layer and will quantified using Image J. Fluorescent images were acquired by Olympus Fluoview FV1000 confocal microscope.

Statistics

Data are presented as mean±SEM. All in vitro experiments are representative of 3 independent experiments. Data were subjected to Student's t-test and P<0.05 was considered statistically significant.

Example 1. MiR-26a is Increased in Response to High Glucose in ECs

Figure 1B:
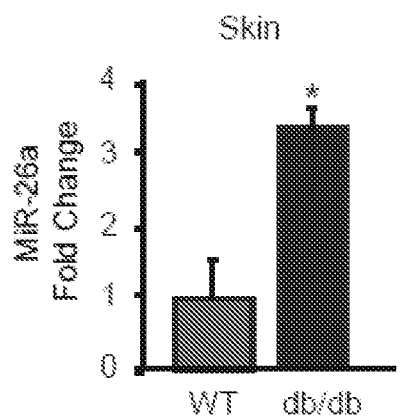

To explore if miR-26a expression is altered in response to diabetic stimuli in ECs, we first examined miR-26a expression in ECs treated with D-glucose. MiR-26a expression was increased by 2.4-fold and 1.2-fold in response to D-glucose in HUVECs and HMVECs, respectively, compared to control cells (FIG. 1A). We also examined miR-26a expression in the wounds of db/db mice. Similar to our in vitro findings, miR-26a expression was 3.5-fold higher in db/db mice compared to WT mice 4 days post-wounding (FIG. 1B). These data suggest that miR-26a may be involved in the earlier pathogenesis of endothelial dysfunction and angiogenesis in response to diabetic stimuli in dermal wound healing.

Figure 2A:
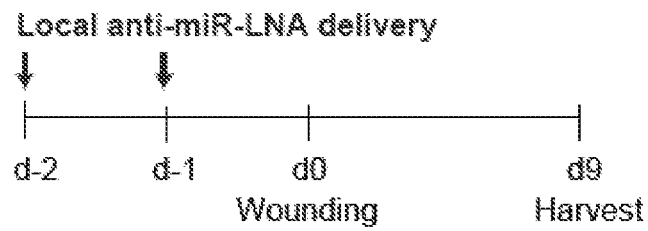
FIGS. 2A-E. LNA-anti-miR-26a delivery to db/db mice promotes wound healing. (A) After two local injections in mice of LNA-anti-miR-26a (MiR-26a$_i$) or scrambled non-specific control LNA-antimiRs (NS$_i$) (n=11-12 per group), mice underwent dorsal skin wounding. (B-E) Wound analyses included: miR-26a expression quantified by RT-qPCR (B) granulation tissue thickness (GTT) (C) wound closure areas (D) and confocal immunofluorescence staining for CD31 and isolectin (E). Scale bars, 125 µm (C) and 5 mm (D) and 100 µm (E) All data represent means±s.e.m. *P<0.05, ***P<0.001.
Figure 2B:
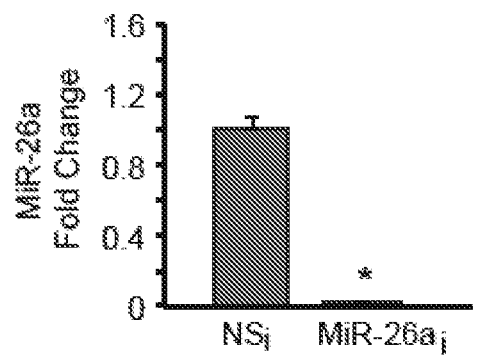
Figure 2C:
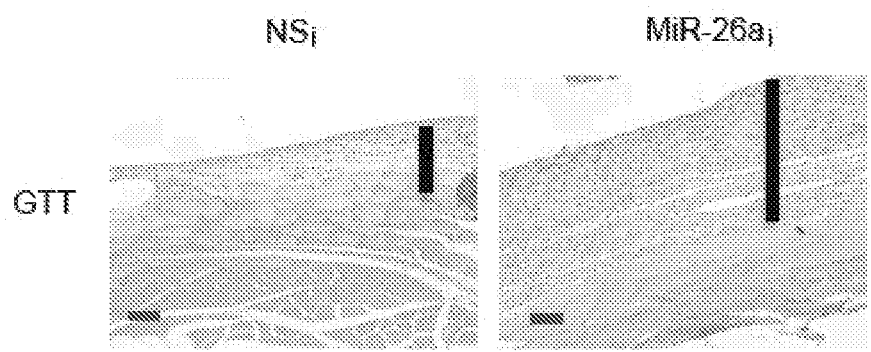
Figure 2C:
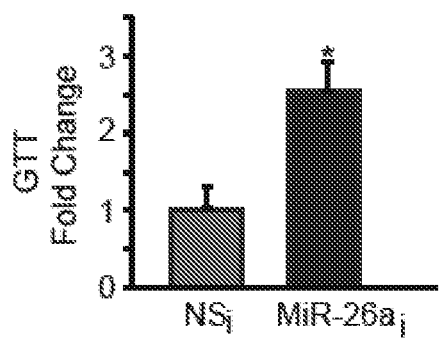
Figure 2D:
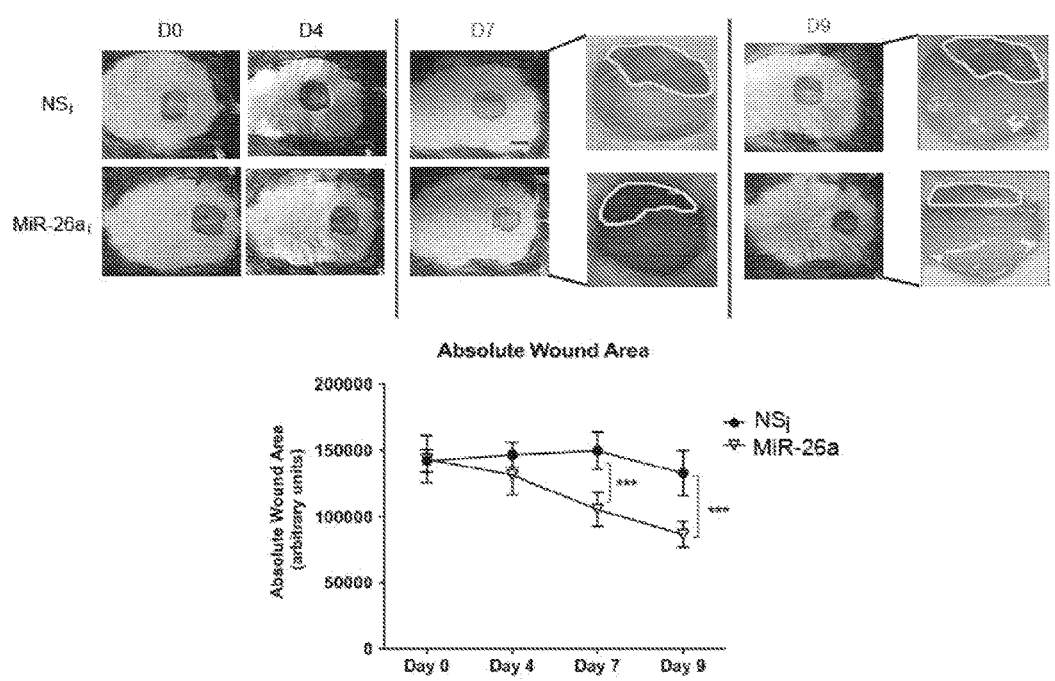
Figure 2E:
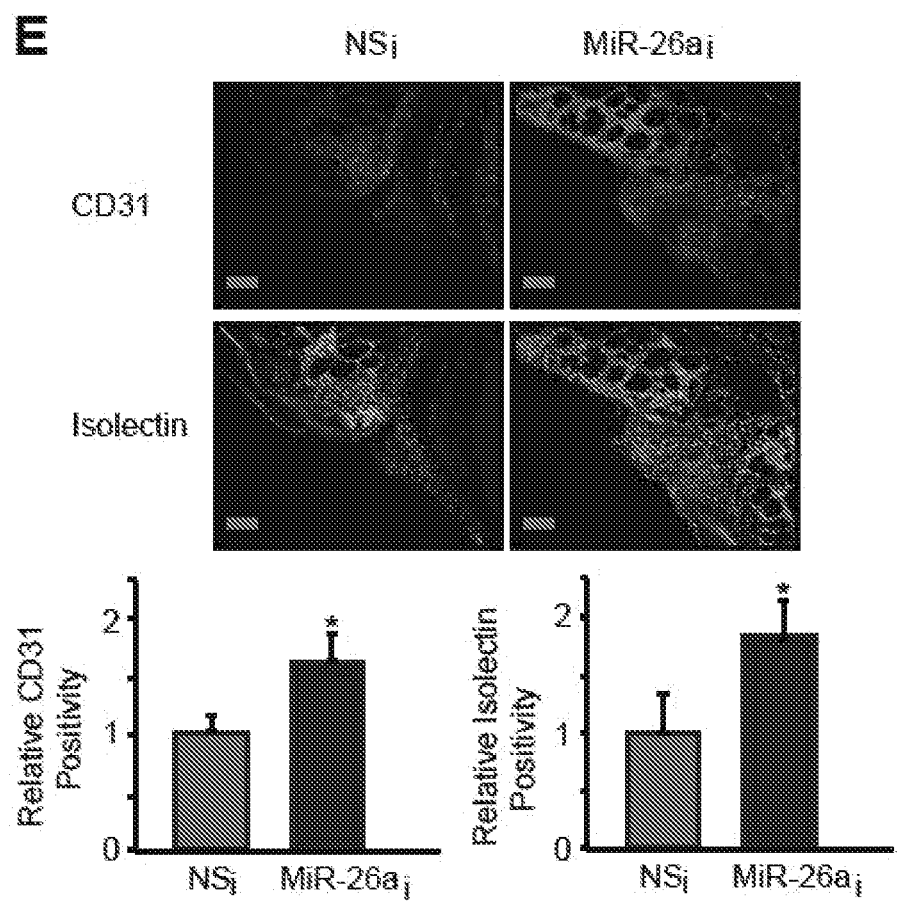

Example 2. Inhibition of miR-26a Promotes Wound Healing and Angiogenesis In Vivo To understand the role of miR-26a in diabetic dermal wound healing, we neutralized miR-26a expression in db/db mice by direct local intradermal injection of 50 µM of anti-miR-26a-LNA twice followed by punch biopsy wounding of the skin on the dorsal surface of the mice (FIG. 2A). MiR-26a expression was effectively suppressed by >99% ($p<0.001$) in the dermal wounds (FIG. 2B) and resulted in a 2.5-fold increase in granulation tissue thickness over control injections after 9 days (FIG. 2C). Remarkably, therapeutic inhibition of miR-26a potently increased wound closure by 53% (FIG. 2D), an effect associated with the induction of robust angiogenesis as demonstrated by increased staining for CD31-positive cells by 1.6-fold and for isolectin-positive cells by 1.8-fold compared to non-specific, scrambled anti-miR controls (FIG. 2E). Collectively these data indicate that inhibition of miR-26a strongly promotes diabetic dermal wound healing and angiogenesis.

Example 3. MiR-26a Deficiency Rescues Impaired Growth and Migration in ECs but not in Fibroblasts Dermal wound healing involves a coordinating effort by several cell types including endothelial cells, fibroblasts, keratinocytes, and leukocytes[19]. To explore the functional role of miR-26a in specific cell types relevant to wound healing, we inhibited the expression of miR-26a in human dermal microvascular endothelial cells (HMVECs), human umbilical vein endothelial cells (HUVECs), and human dermal fibroblasts (HDFs) in the presence and absence of a diabetic stimuli. Interestingly, while inhibition of miR-26a rescued impaired growth and migration in the presence of high glucose in HUVECs (FIGS. 3A and 3B) and HMVECs (FIGS. 3C and 3D), there were minimal effects of anti-miR-26a on fibroblast or keratinocyte growth or migration in the presence of high glucose (FIG. 3E-F and FIGS. 6A-C). In addition, we observed only modest changes in smooth muscle α-actin (SMA-α-actin) and collagen deposition in the diabetic dermal wounds in response to miR-26a neutralization (FIG. 3G and FIG. 7). Taken together, these data suggest that miR-26a inhibition may mediate cell-specific functional effects in response to diabetic stimuli.

Example 4. MiR-26a Targets SMAD1 Signaling in ECs

We previously have demonstrated that miR-26a exerts its effects on EC growth and angiogenesis through the regulation of the BMP/SMAD1/Id1 signaling pathway.[20] Interestingly, miR-26a inhibits SMAD1 expression induced by diabetic stimuli in HUVECs (FIG. 4A). To further examine miR-26a regulation of SMAD1 signaling in the context of diabetic wound healing, we evaluated SMAD1 and its targets ID1 and p27 expression in wounds of db/db mice by local delivery of LNA-anti-miR-miR-26a. As shown in FIG. 4B, both SMAD1 and its target gene ID1 expression were significantly increased, whereas the cell cycle progression gene p27 expression was significantly reduced at the mRNA level. Furthermore SMAD1 expression was increased at the protein level (FIG. 4C) and it co-localized with CD31-positive cells in the wounds of db/db mice by confocal immunofluorescence staining (FIG. 4D). Collectively, these results indicate that miR-26a targets SMAD1 signaling in diabetic dermal wounds and that miR-26a neutralization restores EC growth and angiogenic function.

Figure 5A:
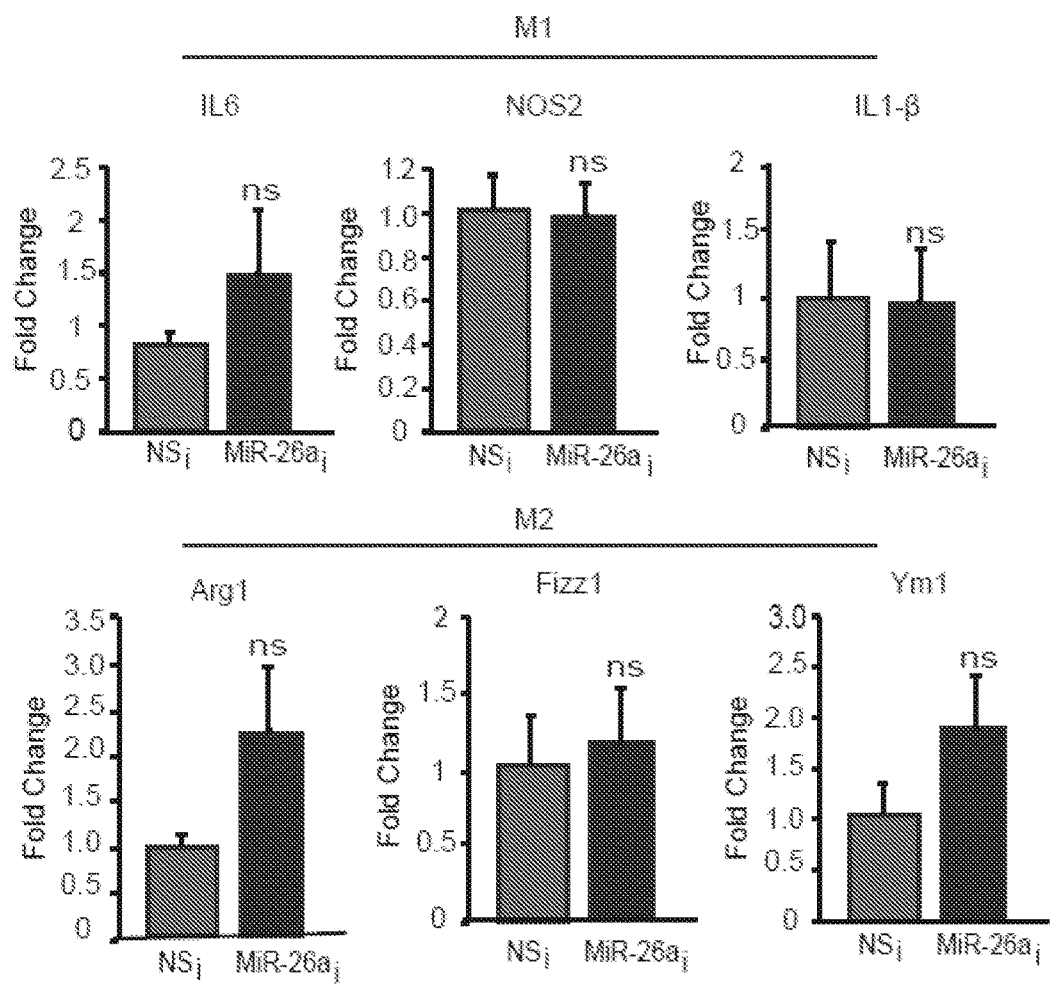
FIGS. 5A-B. Neutralization of miR-26a has no effect on M1 and M2 macrophage accumulation in diabetic dermal wounds. After two local injections in mice of LNA-anti-miR-26a (MiR-26a$_i$) or scrambled non-specific control LNA-antimiRs (NS$_i$) (n=11-12 per group), mice underwent dorsal skin wounding. (A-B) Wound analyses included: (A) Expression of M1 and M2 macrophage markers quantified by RT-qPCR; and (B) confocal immunofluorescence staining for CCR7 (red), CD68 (green) and DAPI (blue) for M1 and CD206 (red), CD68 (green) and DAPI (blue) for M2 macrophages. Scale bar 100 µm. All data represent means±s.e.m.
Figure 5B:
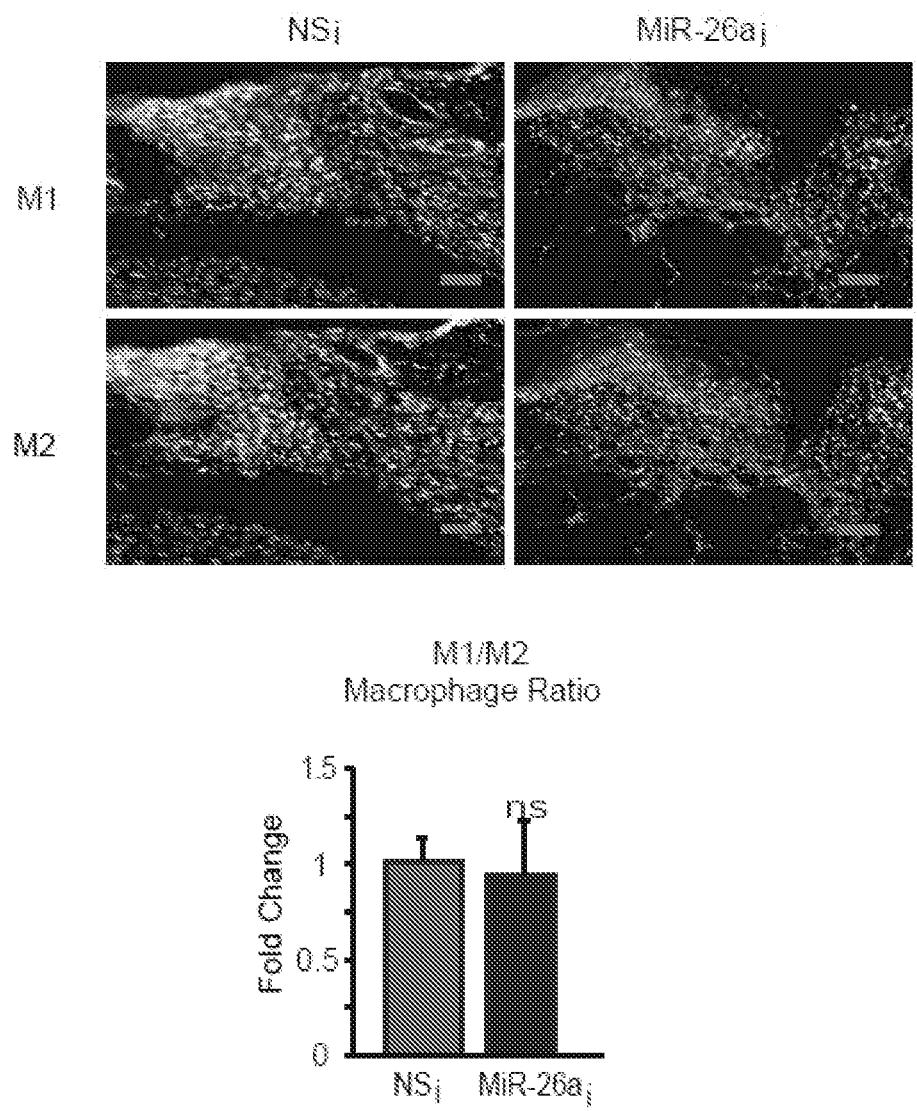
Figure 6A:
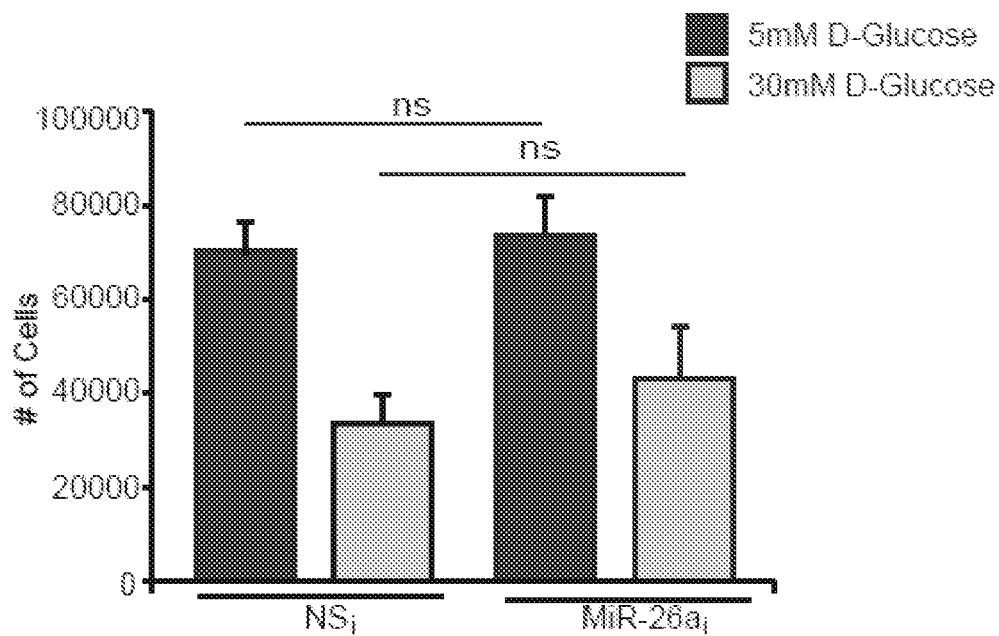
Figure 6A:
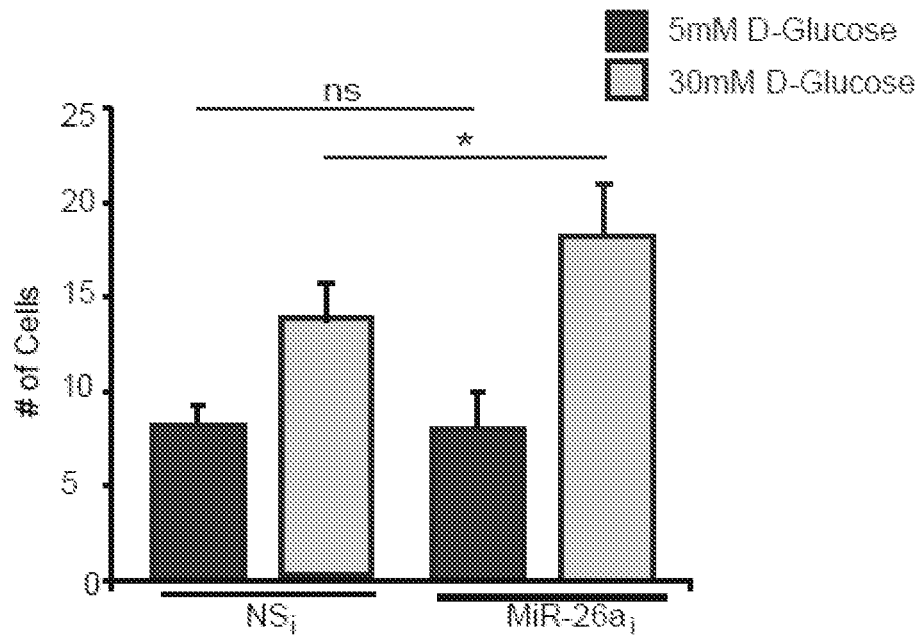
Figure 8:
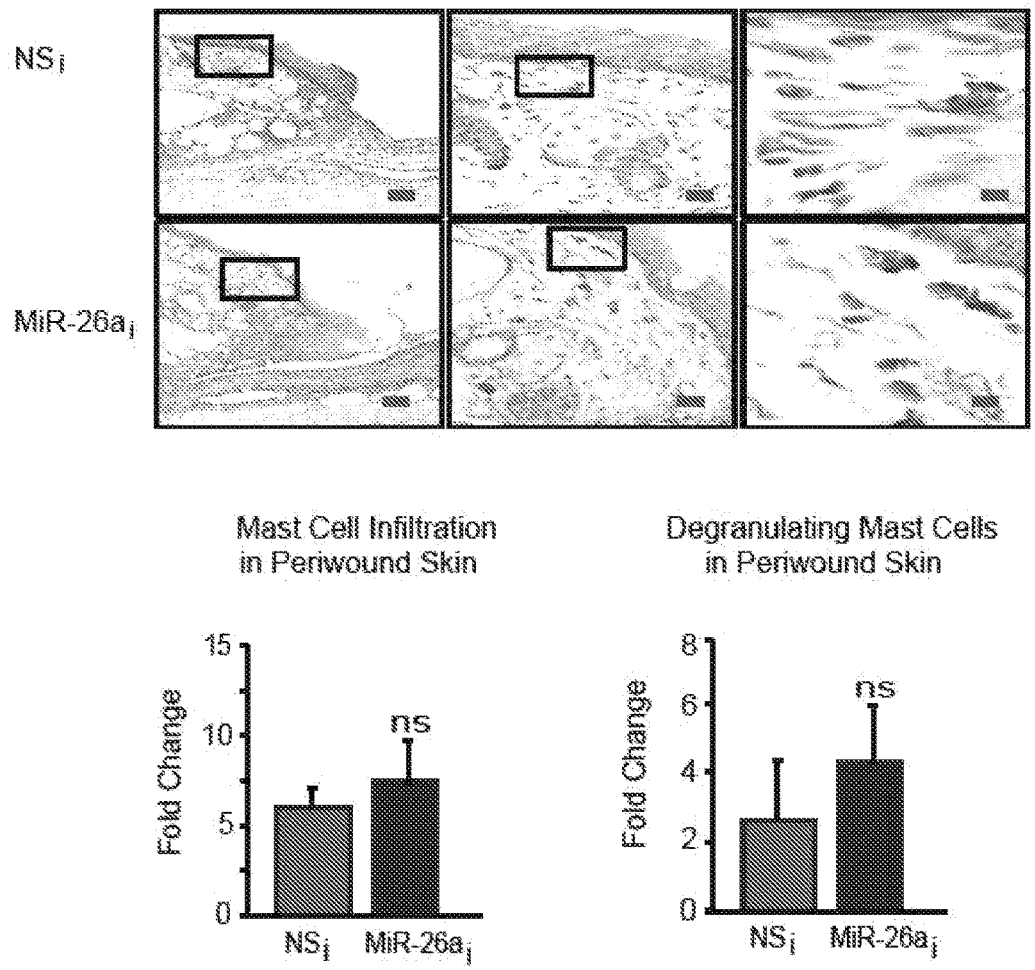
FIG. 8. MiR-26a deficiency has no effect on Mast Cell Infiltration. After two local injections of LNA-anti-miR-26a, db/db mice were wounded by punch biopsy on the upper back and the wounds were collected on day 9 for Toluidine Blue immunostaining. Scale bar 100 µm. Results are representative of n=7-9 replicates per group. All data represent means±s.e.m.

Example 5. Neutralization of miR-26a has No Effect on M1 and M2 Macrophages or Mast Cells in Diabetic Dermal Wounds Macrophages play an important role in mediating dermal wound healing. For example, depletion of macrophages delayed re-epithelialization, reduced collagen deposition, and impaired angiogenesis.[21-23] To explore whether inhibition of miR-26a in diabetic wounds effect the classically activated pro-inflammatory M1 or the alternatively-activated M2 macrophage subset, we studied the expression markers of these macrophage in wounds of diabetic mice. There was no significant effect of miR-26a neutralization on gene expression profiles of M1 or M2 markers (FIG. 5A). In addition, we did not observe a switch from M1 to M2 phenotype by evaluating M1 marker CCR7 and the M2 marker CD206 by immunostaining (FIG. 5B). Similarly, toluidine blue staining for mast cells demonstrated no differences in the accumulation of mast cells or their degranulation in response to local neutralization of miR-26a compared to NS controls (FIG. 8). Collectively, these data suggest that while inhibition of miR-26a promotes wound closure, it does not modify M1/M2 polarization or mast cell accumulation in diabetic wounds.

REFERENCES

1. Trautner C, Haastert B, Giani G, Berger M. Amputations and diabetes: A case-control study. Diabet Med. 2002; 19:35-40
2. Erba P, Ogawa R, Ackermann M, Adini A, Miele L F, Dastouri P, Helm D, Mentzer S J, D'Amato R J, Murphy G F, Konerding M A, Orgill D P. Angiogenesis in wounds treated by microdeformational wound therapy. Ann Surg. 2011; 253:402-409
3. Greene A K, Puder M, Roy R, Arsenault D, Kwei S, Moses M A, Orgill D P. Microdeformational wound therapy: Effects on angiogenesis and matrix metalloproteinases in chronic wounds of 3 debilitated patients. Ann Plast Surg. 2006; 56:418-422
4. Peng C, Chen B, Kao H K, Murphy G, Orgill D P, Guo L. Lack of fgf-7 further delays cutaneous wound healing in diabetic mice. Plast Reconstr Surg. 2011; 128:673e-684e
5. Song G, Nguyen D T, Pietramaggiori G, Scherer S, Chen B, Zhan Q, Ogawa R, Yannas I V, Wagers A J, Orgill D P, Murphy G F. Use of the parabiotic model in studies of cutaneous wound healing to define the participation of circulating cells. Wound Repair Regen. 2010; 18:426-432
6. Potente M, Gerhardt H, Carmeliet P. Basic and therapeutic aspects of angiogenesis. Cell. 2011; 146:873-887
7. Falanga V. Wound healing and its impairment in the diabetic foot. Lancet. 2005; 366:1736-1743
8. Bonauer A, Boon R A, Dimmeler S. Vascular micrornas. Curr Drug Targets. 2010; 11:943-949
9. Sayed D, Abdellatif M. Micrornas in development and disease. Physiol Rev. 2011; 91:827-887
10. Wang S, Aurora A B, Johnson B A, Qi X, McAnally J, Hill J A, Richardson J A, Bassel-Duby R, Olson E N. The endothelial-specific microrna mir-126 governs vascular integrity and angiogenesis. Dev Cell. 2008; 15:261-271
11. Bonauer A, Carmona G, Iwasaki M, Mione M, Koyanagi M, Fischer A, Burchfield J, Fox H, Doebele C, Ohtani K, Chavakis E, Potente M, Tjwa M, Urbich C, Zeiher A M, Dimmeler S. Microrna-92a controls angiogenesis and functional recovery of ischemic tissues in mice. Science. 2009; 324:1710-1713
12. Fasanaro P, D'Alessandra Y, Di Stefano V, Melchionna R, Romani S, Pompilio G, Capogrossi M C, Martelli F. Microrna-210 modulates endothelial cell response to hypoxia and inhibits the receptor tyrosine kinase ligand ephrin-a3. J Biol Chem. 2008; 283:15878-15883
13. Chen Y, Gorski D H. Regulation of angiogenesis through a microrna (mir-130a) that down-regulates antiangiogenic homeobox genes gax and hoxa5. Blood. 2008; 111:1217-1226
14. Zhou Q, Gallagher R, Ufret-Vincenty R, Li X, Olson E N, Wang S. Regulation of angiogenesis and choroidal neovascularization by members of microrna-23~27~24 clusters. Proc Natl Acad Sci USA. 2011; 108:8287-8292
15. Suarez Y, Fernandez-Hernando C, Pober J S, Sessa W C. Dicer dependent micrornas regulate gene expression and functions in human endothelial cells. Circ Res. 2007; 100:1164-1173
16. Menghini R, Casagrande V, Cardellini M, Martelli E, Terrinoni A, Amati F, Vasa-Nicotera M, Ippoliti A, Novelli G, Melino G, Lauro R, Federici M. Microrna 217 modulates endothelial cell senescence via silent information regulator 1. Circulation. 2009; 120:1524-1532
17. Chan Y C, Roy S, Khanna S, Sen C K. Downregulation of endothelial microrna-200b supports cutaneous wound angiogenesis by desilencing gata binding protein 2 and vascular endothelial growth factor receptor 2. Arteriosclerosis, thrombosis, and vascular biology. 2012; 32:1372-1382
18. Caporali A, Meloni M, Vollenkle C, Bonci D, Sala-Newby G B, Addis R, Spinetti G, Losa S, Masson R, Baker A H, Agami R, le Sage C, Condorelli G, Madeddu P, Martelli F, Emanueli C. Deregulation of microrna-503 contributes to diabetes mellitus-induced impairment of endothelial function and reparative angiogenesis after limb ischemia. Circulation. 2011; 123:282-291
19. Barrientos S, Stojadinovic O, Golinko M S, Brem H, Tomic-Canic M. Growth factors and cytokines in wound healing. Wound Repair Regen. 2008; 16:585-601
20. Icli B, Wara A K, Moslehi J, Sun X, Plovie E, Cahill M, Marchini J F, Schissler A, Padera R F, Shi J, Cheng H W, Raghuram S, Arany Z, Liao R, Croce K, Macrae C A, Feinberg M W. Microrna-26a regulates pathological and physiological angiogenesis by targeting bmp/smad1 signaling. Circ Res. 2013
21. Lucas T, Waisman A, Ranjan R, Roes J, Krieg T, Muller W, Roers A, Eming S A. Differential roles of macrophages in diverse phases of skin repair. J Immunol. 2010; 184: 3964-3977
22. Mirza R, DiPietro L A, Koh T J. Selective and specific macrophage ablation is detrimental to wound healing in mice. The American journal of pathology. 2009; 175: 2454-2462
23. Maruyama K, Asai J, Ii M, Thorne T, Losordo D W, D'Amore P A. Decreased macrophage number and activation lead to reduced lymphatic vessel formation and contribute to impaired diabetic wound healing. The American journal of pathology. 2007; 170:1178-1191
24. White R, McIntosh C. Topical therapies for diabetic foot ulcers: Standard treatments. Journal of wound care. 2008; 17:426, 428-432
25. Blakytny R, Jude E. The molecular biology of chronic wounds and delayed healing in diabetes. Diabetic medicine: a journal of the British Diabetic Association. 2006; 23:594-608
26. Watanabe Y, Lee S W, Detmar M, Ajioka I, Dvorak H F. Vascular permeability factor/vascular endothelial growth factor (vpf/vegf) delays and induces escape from senescence in human dermal microvascular endothelial cells. Oncogene. 1997; 14:2025-2032
27. Cross M J, Claesson-Welsh L. Fgf and vegf function in angiogenesis: Signalling pathways, biological responses and therapeutic inhibition. Trends in pharmacological sciences. 2001; 22:201-207
28. Galiano R D, Tepper O M, Pelo C R, Bhatt K A, Callaghan M, Bastidas N, Bunting S, Steinmetz H G, Gurtner G C. Topical vascular endothelial growth factor accelerates diabetic wound healing through increased angiogenesis and by mobilizing and recruiting bone marrow-derived cells. The American journal of pathology. 2004; 164:1935-1947
29. Kolluru G K, Bir S C, Kevil C G. Endothelial dysfunction and diabetes: Effects on angiogenesis, vascular remodeling, and wound healing. International journal of vascular medicine. 2012; 2012:918267
30. Brem H, Jacobs T, Vileikyte L, Weinberger S, Gibber M, Gill K, Tarnovskaya A, Entero H, Boulton A J. Wound-healing protocols for diabetic foot and pressure ulcers. Surgical technology international. 2003; 11:85-92
31. Miyazono K, Miyazawa K. Id: A target of bmp signaling. Science's STKE: signal transduction knowledge environment. 2002; 2002:pe40
32. Goumans M J, Valdimarsdottir G, Itoh S, Rosendahl A, Sideras P, ten Dijke P. Balancing the activation state of the endothelium via two distinct tgf-beta type i receptors. The EMBO journal. 2002; 21:1743-1753
33. Norton J D, Deed R W, Craggs G, Sablitzky F. Id helix-loop-helix proteins in cell growth and differentiation. Trends in cell biology. 1998; 8:58-65
34. Dang X, Ma A, Yang L, Hu H, Zhu B, Shang D, Chen T, Luo Y. Microrna-26a regulates tumorigenic properties of ezh2 in human lung carcinoma cells. Cancer genetics. 2012; 205:113-123
35. Shilo S, Roy S, Khanna S, Sen C K. Microrna in cutaneous wound healing: A new paradigm. DNA and cell biology. 2007; 26:227-237
36. van Solingen C, Araldi E, Chamorro-Jorganes A, Fernandez-Hernando C, Suarez Y. Improved repair of dermal wounds in mice lacking microrna-155. Journal of cellular and molecular medicine. 2014
37. Jin Y, Tymen S D, Chen D, Fang Z J, Zhao Y, Dragas D, Dai Y, Marucha P T, Zhou X. Microrna-99 family targets akt/mtor signaling pathway in dermal wound healing. PloS one. 2013; 8:e64434

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of promoting diabetic dermal wound healing in a subject, the method comprising:
   selecting a subject with diabetes and a dermal wound; and
   administering to cells in or surrounding the wound of the subject a therapeutically effective amount of an inhibitor of microRNA-26a (miR-26a).

2. The method of claim 1, wherein the inhibitor of miR-26a is an inhibitory nucleic acid.

3. The method of claim 2, wherein the inhibitory nucleic acid is an antisense nucleic acid, small interfering RNA (siRNA), or small hairpin RNA (shRNA).

4. The method of claim 2 wherein the inhibitory nucleic acid is modified.

5. The method of claim 4, wherein the modified inhibitory nucleic acid comprises one or more of phosphorothioate bonds, methylphosphonate bonds, peptide nucleic acids, or locked nucleic acid (LNA) molecules.

6. The method of claim 1, wherein the inhibitor is administered locally to the wound.

7. The method of claim 6, wherein the inhibitor is administered by injection into the wound or by topical administration onto the wound.

8. A method of treating a dermal wound in a subject with diabetes, the method comprising:
   selecting a subject with diabetes and a dermal wound; and
   administering a therapeutically effective amount of an inhibitor of microRNA-26a (miR-26a) to cells in or surrounding the wound.

9. The method of claim 8, wherein the inhibitor of miR-26a is an inhibitory nucleic acid.

10. The method of claim 9, wherein the inhibitory nucleic acid is an antisense nucleic acid, small interfering RNA (siRNA), or small hairpin RNA (shRNA).

11. The method of claim 9, wherein the inhibitory nucleic acid is modified.

12. The method of claim 11, wherein the modified inhibitory nucleic acid comprises one or more of phosphorothioate bonds, methylphosphonate bonds, peptide nucleic acids, or locked nucleic acid (LNA) molecules.

13. The method of claim 8, wherein the inhibitor is administered locally to the wound.

14. The method of claim 13, wherein the inhibitor is administered by injection into the wound or by topical administration onto the wound.

* * * * *

SEQUENCE LISTING

```
<160> NUMBER OF SEQ ID NOS: 4

<210> SEQ ID NO 1
<211> LENGTH: 22
<212> TYPE: RNA
<213> ORGANISM: Homo sapiens

<400> SEQUENCE: 1
uucaaguaau ccaggauagg cu                                                22

<210> SEQ ID NO 2
<211> LENGTH: 77
<212> TYPE: RNA
<213> ORGANISM: Homo sapiens

<400> SEQUENCE: 2
guggccucgu ucaaguaauc caggauaggc ugugcagguc ccaaugggcc uauucuuggu       60
uacuugcacg gggacgc                                                     77

<210> SEQ ID NO 3
<211> LENGTH: 84
<212> TYPE: RNA
<213> ORGANISM: Homo sapiens

<400> SEQUENCE: 3
ggcuguggcu ggauucaagu aauccaggau aggcuguuuc caucugugag gccuauucuu       60
gauuacuugu uucuggaggc agcu                                             84

<210> SEQ ID NO 4
<211> LENGTH: 7
<212> TYPE: RNA
<213> ORGANISM: Homo sapiens

<400> SEQUENCE: 4 uucaagu                                                                 7
```